United States Patent
Kim et al.

(10) Patent No.: US 12,201,798 B2
(45) Date of Patent: Jan. 21, 2025

(54) METHOD FOR INCREASING CELL VIABILITY BY USING DRUG DELIVERY SYSTEM AND ULTRASOUND IRRADIATION, AND ULTRASOUND IRRADIATION APPARATUS USING SAME

(71) Applicant: BIOINFRA LIFE SCIENCE INC., Seoul (KR)

(72) Inventors: Chul Woo Kim, Seoul (KR); Dong Hee Park, Seoul (KR); Jong Ho Won, Seoul (KR); Hea Ry Oh, Seoul (KR)

(73) Assignee: BioInfra Life Science Inc., Seoul (KR)

( * ) Notice: Subject to any disclaimer, the term of this patent is extended or adjusted under 35 U.S.C. 154(b) by 808 days.

(21) Appl. No.: 17/290,511

(22) PCT Filed: Oct. 31, 2019

(86) PCT No.: PCT/KR2019/014616
§ 371 (c)(1),
(2) Date: Apr. 30, 2021

(87) PCT Pub. No.: WO2020/091466
PCT Pub. Date: May 7, 2020

(65) Prior Publication Data
US 2022/0008705 A1    Jan. 13, 2022

(30) Foreign Application Priority Data

Oct. 31, 2018  (KR) .................. 10-2018-0132628
Oct. 31, 2019  (KR) .................. 10-2019-0137553

(51) Int. Cl.
*A61N 7/00*   (2006.01)
*A61K 31/353* (2006.01)
(Continued)

(52) U.S. Cl.
CPC ....... *A61M 37/0092* (2013.01); *A61K 31/353* (2013.01); *A61K 45/06* (2013.01); *A61N 7/00* (2013.01); *A61N 2007/0034* (2013.01)

(58) Field of Classification Search
CPC .......... A61M 37/0092; A61M 37/0007; A61N 7/00; A61N 2007/0034
See application file for complete search history.

(56) References Cited

U.S. PATENT DOCUMENTS 7,004,933 B2 *  2/2006  McDaniel ......... A61M 37/0092
                                                          604/506
2003/0009153 A1 * 1/2003 Brisken ............ A61M 37/0092
                                                        604/890.1
(Continued)

FOREIGN PATENT DOCUMENTS

KR    1020170104425 A      9/2017
WO    WO-0132232 A2 *      5/2001 ........ A61M 37/0092

OTHER PUBLICATIONS

Jan. 2014, pp. 145 (Son, Jung-woo. Optimization of the Parameter for Transdermal Drug Delivery by Ultrasound with an Ultrasound Contrast Agent and Quantitative Analysis. Master's thesis, Department of Biomedical Engineering, the Graduate School of Yonsei University.) See pp. 20-38; figures 3-3, 4-3-4-5; table 3-2. (55 pages).
Park et al., 2012 "Sonophoresis Using Ultrasound Contrast Agents for Transdermal Drug Delivery: An In Vivo Experimental Study," Ultrasound in Med & Biol 38(4):642-50.

(Continued)

*Primary Examiner* — Laura A Bouchelle
(74) *Attorney, Agent, or Firm* — Husch Blackwell LLP

(57) ABSTRACT

Disclosed are a method for increasing the viability of cells by ultrasound irradiation and an ultrasound irradiation apparatus using same. The method comprises: applying a drug and an epidermal drug delivery system onto the epidermis of (Continued)

a subject; and, with ultrasound parameters each being preset within a certain range, an ultrasound irradiation apparatus irradiating ultrasound onto the epidermis of the subject through an ultrasound generation unit placed within a critical range from the epidermis of the subject, wherein the epidermal drug delivery system induces the formation of cavities, i.e., cavitation around the epidermis of the subject when the ultrasound is irradiated, the ultrasound parameters at least include an ultrasound pressure and an ultrasound duty percentage, the ultrasound pressure is 0.5-1 MPa, and the ultrasound duty percentage is 1-5%.

10 Claims, 50 Drawing Sheets

(51) Int. Cl.
*A61K 45/06* (2006.01)
*A61M 37/00* (2006.01)

(56) References Cited

U.S. PATENT DOCUMENTS

| 2005/0283110 A1 | 12/2005 | Atala et al. |
| 2008/0319375 A1 | 12/2008 | Hardy |
| 2009/0318853 A1* | 12/2009 | Reed .................. A61N 7/00 601/2 |
| 2017/0216177 A1* | 8/2017 | Thrower .............. A61K 8/9767 |
| 2018/0169013 A1 | 6/2018 | Seo et al. |

OTHER PUBLICATIONS

[Online post] Redensvl-the hair growth galvanizer. Cosmetics Business [Online]. 3-4,8,11-12,16 Mar. 14, 2014, [Retrieved on Feb. 9, 2020], Retrieved from <URL:littps://www.cosineticsbusiness.com/news/articlepage/Redensyl_the_hair_growth_galvanizer/9671'7>See pp. 1-3 (6 pages).

International Search Report from related International Application No. PCT/KR2019/014616, mailed Feb. 14, 2020 (7 pages).

Written Opinion from related International Application No. PCT/KR2019/014616, mailed Feb. 14, 2020 (8 pages).

* cited by examiner

PERIOD = 1/FREQUENCY

PERIOD = $T_{ON} + T_{OFF}$

DUTY PERCENTAGE = $T_{ON}/(T_{ON}+T_{OFF})*100$

METHOD FOR INCREASING CELL VIABILITY BY USING DRUG DELIVERY SYSTEM AND ULTRASOUND IRRADIATION, AND ULTRASOUND IRRADIATION APPARATUS USING SAME

1. FIELD OF THE DISCLOSURE

The present disclosure relates to a method for increasing a viability of cells by irradiating the cells with ultrasound and an ultrasound irradiating device using the same.

2. BACKGROUND OF THE DISCLOSURE

Minoxidil and Propecia are substances used as hair growth promoters. Minoxidil is a formulation applied to a scalp, and was developed by Pfizer as a treatment for hypertension due to its vasodilating effect, but is marketed as a hair loss treatment after a study on side effects of hair development on a forehead or a back of a hand. The mechanism by which minoxidil promotes hair growth is not fully understood, but it is theoretically known that minoxidil widens blood vessels in the scalp, opens potassium channels in cell membranes, and provides more oxygen and nutrients to follicles and thus inhibits hair loss, promotes hair growth, and thickens hair. But common side effects include redness, dry scalp, heart palpitations, tachycardia, and arrhythmia, etc.

Propecia sold by Merck is a brand name of finasteride which was originally developed to treat prostatic hyperplasia, but is used as the hair loss treatment because it promotes hair growth. 5α-reductase converts testosterone, i.e., male hormone, into dihydrotestosterone (DHT) which plays a major role in causing the hair loss. Finasteride reduces concentration of DHT that causes the hair loss by inhibiting the 5α-reductase enzyme. Typical side effects include decreased sexual functions, such as impotence, decreased libido, and a sexual arousal disorder, etc., and dizziness, a headache, a swelling, and a skin rash, etc. Men with infertility or low sperm count should pay attention to taking the drugs. In addition, there is a risk of birth defects, so women of childbearing age should not take or contact the drugs, and there are restrictions on prescription.

In addition, Avodart is a brand name of dutasteride family and, like finasteride, was developed as a treatment for the prostatic hyperplasia, but has been found to have an effect of preventing hair loss and is used as the hair loss treatment. In general, dutasteride is known to have a slightly stronger inhibitory effect against the hair loss than finasteride does. However, side effects such as the decreased libido, decreased kidney functions etc. are also known to be strong, so it is used less than finasteride, and has not been approved by the FDA as the hair loss treatment in the United States.

In view of the side effects of the drugs, it is urgent to develop a system that efficiently prevents the hair loss, increases hair thickness, and promotes blackening of hair while minimizing the side effects on the scalp and human body.

There are a number of raw materials included in functional cosmetics for preventing the hair loss, such as Redensyl, but those are peptides and growth factors, and most of them have high molecular weights (for example, 0.5 to 10 kDa). Therefore, when applied directly to a skin, the raw materials do not penetrate the skin well enough due to its low skin absorption rate.

Even if an existing drug delivery system (DDS) is used, only raw materials with low molecular weights (<500 Da) are partially absorbed due to the low skin absorption rate. Also, a deviation in the absorption rate is large depending on characteristics, such as hydrophilicity, hydrophobicity or poor solubility, etc., of the raw materials.

Iontophoresis is a technology that promotes absorption of drugs by using a potential difference generated by microcurrent through a means such as a patch at an application site. Although the technology has wide application, is non-invasive and painless, there may be limitations in the application when a polarity of the drug is not sufficiently strong, and there may also be limitations in a size or depth of the application of the drug. In addition, if the applied current is too strong, side effects such as erythema, itchiness, etc. may occur.

Microneedles deliver drugs by creating holes hundreds of micrometers deep in the skin. In addition, a laser system can apply the substance for preventing the hair loss to a patient's skin by dermabrasion by a depth of about 5-10 micrometers through laser irradiation, however, it may cause pain and the erythema by irritating the skin. In addition, it has a disadvantage in that it is difficult to apply repeatedly and difficult to apply to a large area.

Considering such limitations of the drug delivery system, there is a need for a method of increasing viability of cells without any side effects in a non-invasive and painless manner within a short time of application by using minimal amounts of the drugs.

3. SUMMARY OF THE DISCLOSURE

It is an object of the present invention to solve all the aforementioned problems.

It is another object of the present disclosure to increase viability of one or more cells in a non-invasive and painless manner by irradiating the cells with ultrasound.

It is still another object of the present disclosure to further increase the viability of the cells by using a drug together with an epidermal drug carrier and the ultrasound compared to a case of only using the drug with a same concentration.

In order to accomplish objects above and characteristic effects to be described later of the present disclosure, distinctive structures of the present disclosure are described as follows.

In accordance with one aspect of the present disclosure, there is provided a method for increasing a viability of one or more cells by irradiating the cells with ultrasound, including steps of: on condition that a drug and an epidermal drug carrier are applied on epidermis of a subject and that ultrasound parameters have been preset within respective ranges, an ultrasound irradiating device positioning an ultrasonic transducer within a threshold range from the epidermis of the subject and then irradiating the epidermis with the ultrasound, wherein the epidermal drug carrier causes cavitation to create at least one cavity around the epidermis in response to irradiating the epidermis with the ultrasound, and wherein the ultrasound parameters include pressure of the ultrasound and duty percentage of the ultrasound, wherein the pressure of the ultrasound ranges from 0.5 MPa to 1 MPa, and wherein the duty percentage of the ultrasound ranges from 1% to 5%.

As one example, the ultrasound parameters further include a pressure of the ultrasound, a duty percentage of the ultrasound, and an intensity of the ultrasound, and wherein the pressure ranges from 0.5 MPa to 1 MPa, the duty percentage ranges from 1% to 5%, and the intensity ranges from 166.7 mW/cm2 to 416.7 mW/cm2.

As one example, the drug is Redensyl.

As one example, a concentration of the Redensyl ranges from 0.5% to 1%.

As one example, the ultrasound parameters further include frequency of the ultrasound, and wherein the frequency of the ultrasound ranges from 0.5 MHz to 4.6 MHz.

As one example, the frequency of the ultrasound is 1 MHz.

As one example, the ultrasound parameters further include total irradiation time of the ultrasound, and wherein the total irradiation time is equal to or less than ten minutes.

As one example, the cells are outer root sheath cells.

In accordance with another aspect of the present disclosure, there is provided an ultrasound irradiating device for increasing a viability of one or more cells by irradiating the cells with ultrasound, including: an ultrasound transducer; and a controlling part, on condition that a drug and an epidermal drug carrier are applied on epidermis of a subject and that ultrasound parameters have been preset within respective ranges, for positioning the ultrasonic transducer within a threshold range from the epidermis of the subject and then allowing the ultrasonic transducer to irradiate the epidermis with the ultrasound; and wherein the epidermal drug carrier causes cavitation to create at least one cavity around the epidermis in response to irradiating the epidermis with the ultrasound, and wherein the ultrasound parameters include a pressure of the ultrasound and a duty percentage of the ultrasound, wherein the pressure of the ultrasound ranges from 0.5 MPa to 1 MPa, and wherein the duty percentage of the ultrasound ranges from 1% to 5%.

As one example, the ultrasound parameters further include a pressure of the ultrasound, a duty percentage of the ultrasound, and an intensity of the ultrasound, and wherein the pressure ranges from 0.5 MPa to 1 MPa, the duty percentage ranges from 1% to 5%, and the intensity ranges from 166.7 mW/cm2 to 416.7 mW/cm2.

As one example, the drug is Redensyl.

As one example, a concentration of the Redensyl ranges from 0.5% to 1%.

As one example, the ultrasound parameters further include frequency of the ultrasound, and wherein the frequency of the ultrasound ranges from 0.5 MHz to 4.6 MHz.

As one example, the frequency of the ultrasound is 1 MHz.

As one example, the ultrasound parameters further include total irradiation time of the ultrasound, and wherein the total irradiation time is equal to or less than ten minutes.

As one example, the cells are outer root sheath cells.

4. BRIEF DESCRIPTION OF THE DRAWINGS

5. DETAILED DESCRIPTION OF THE PREFERRED EMBODIMENTS

Figure 1A:
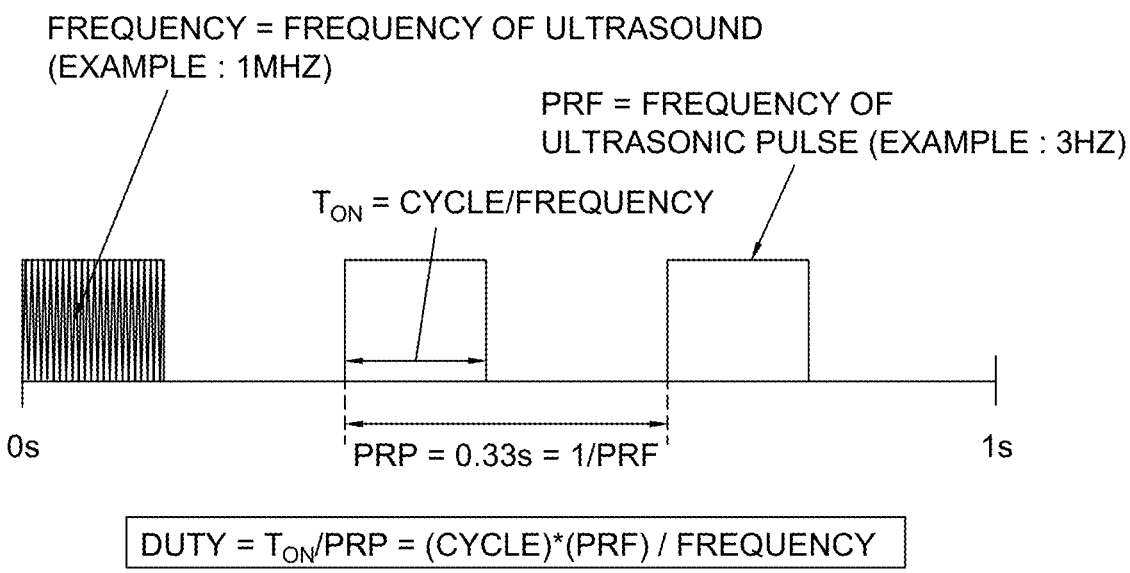
FIGS. 1A and 1B are drawings schematically illustrating ultrasound parameters used in a method for increasing viability of one or more cells by irradiating the cells with ultrasound in accordance with one example embodiment of the present disclosure.

In the following detailed description, reference is made to the accompanying drawings that show, by way of illustration, specific embodiments in which the present disclosure may be practiced. These embodiments are described in sufficient detail to enable those skilled in the art to practice the present disclosure. It is to be understood that the various embodiments of the present disclosure, although different, are not necessarily mutually exclusive. For example, a particular feature, structure, or characteristic described herein in connection with one embodiment may be implemented within other embodiments without departing from the spirit and scope of the present disclosure. In addition, it is to be understood that the position or arrangement of individual elements within each disclosed embodiment may be modified without departing from the spirit and scope of the present disclosure. The following detailed description is, therefore, not to be taken in a limiting sense, and the scope of the present disclosure is defined only by the appended claims, appropriately interpreted, along with the full range of equivalents to which the claims are entitled. In the drawings, like numerals refer to the same or similar functionality throughout the several views.

To allow those skilled in the art to carry out the present disclosure easily, the example embodiments of the present disclosure will be explained in detail by referring to attached diagrams as shown below.

Figure 1B:
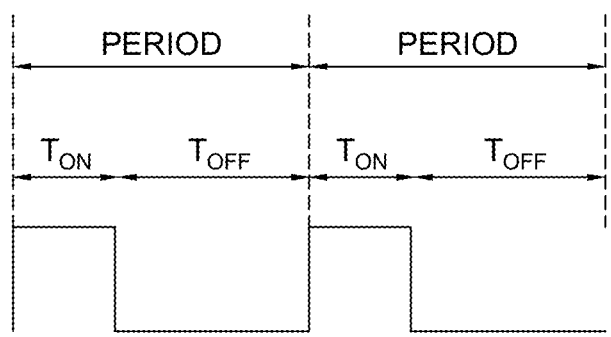

FIGS. 1A and 1B are drawings schematically illustrating ultrasound parameters used in a method for increasing viability of cells by irradiating the cells with ultrasound in accordance with one example embodiment of the present disclosure.

The ultrasound parameters are as follows.

Frequency: a frequency of the ultrasound

Duty percentage: a percentage value of actual time of ultrasound irradiation divided by a period PRF (pulse repetition frequency): the number of times square wave is irradiated per second PRP (pulse repetition period): 1/PRF
Pressure: a pressure of the ultrasound
Intensity=(duty percentage)×pressure$^2$/(2×c×rho): energy of the ultrasound irradiated per unit area (c: speed of sound in water=1,500 m/s, rho: density of water=1,000 kg/m$^3$)

As an example, in FIG. 1A, the square wave of the ultrasound with the frequency of 1 MHz is repeated three times per second, thus PRF is 3 Hz and PRP, i.e., 1/PRF, is 0.3333 second. Herein, a cycle may be a time between an instantaneous peak and its neighboring instantaneous peak in an envelope. Also, in FIG. 1B, the duty percentage is Ton/(Ton+Toff)×100, i.e., a time Ton, during which the actual ultrasound is irradiated, divided by the period Ton+Toff of the ultrasound irradiation.

For reference, a Table 1 below describes intensities according to pressures and duty percentages of the ultrasound.

TABLE 1

| Pressure (MPa) | Intensity (W/m$^2$) | Intensity with 100% duty percentage (W/cm$^2$) | Intensity with 1% duty percentage (mW/cm$^2$) | Intensity with 2% duty percentage (mW/cm$^2$) | Intensity with 3% duty percentage (mW/cm$^2$) | Intensity with 5% duty percentage (mW/cm$^2$) |
|---|---|---|---|---|---|---|
| 0.5 | 83333.3 | 8.3 | 83.3 | 166.7 | 250.0 | 416.7 |
| 0.7 | 163333.3 | 16.3 | 163.3 | 326.7 | 490.0 | 816.7 |
| 1 | 333333.3 | 33.3 | 333.3 | 666.7 | 1000.0 | 1666.7 |

Figure 2:
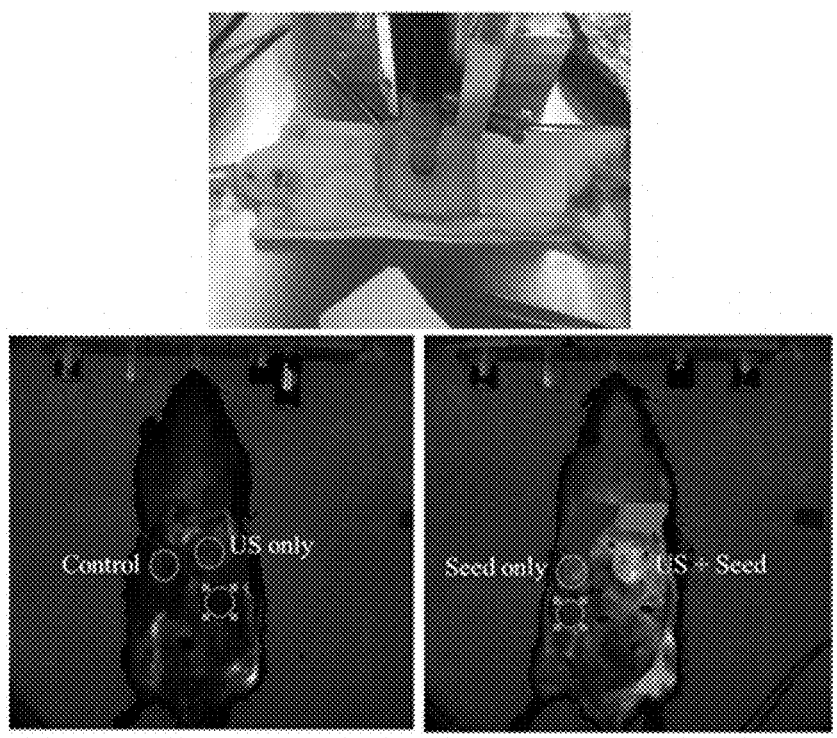
FIG. 2 is a drawing schematically illustrating experimental results of a dermal stability of the method for increasing the viability of the cells by irradiating the cells with the ultrasound in accordance with one example embodiment of the present disclosure.

Next, FIG. 2 is a drawing schematically illustrating experimental results of a dermal stability of the method for increasing the viability of the cells by irradiating the cells with the ultrasound in accordance with one example embodiment of the present disclosure.

Specifically, as a result of monitoring temperature changes during the ultrasound irradiation on a skin of an 8-week-old male rat, it is observed that a skin temperature increased by about 1.2 degrees Celsius after 30 minutes and that 0.05 degrees Celsius per minute was changed in temperature on average. That is, it can be seen that the degree of temperature change due to the ultrasound irradiation does not reach as much extent as it damages the skin.

Next, experimental conditions for observing the viability of the cells according to the ultrasound irradiation are described.

For reference, a Table 2 below describes cell seeding densities.

TABLE 2

| Recommended seeding density | 5*10$^3$ cells/cm$^2$ | |
|---|---|---|
| Dish | Surface area (cm$^2$) | Seeding density |
| 60 mm | 21 | 1.05*10$^5$ cells |
| 100 mm | 55 | 2.75*10$^5$ cells |
| T75 | 75 | 3.75*10$^5$ cells |

Also, a Table 3 below describes required amounts of the cells according to the conditions.

TABLE 3

| | | Ultrasound is irradiated per well for 10 minutes | Number of wells | Number of cells seeding (total amount) | T75 flask |
|---|---|---|---|---|---|
| Cell viability assay | 96 well plate (3*10$^3$ cell/well) | Condition 3 wells | 22 66 | 6.6*10$^4$ 1.98*10$^5$ | 8.4*10$^6$ |
| | 6 well plate (8*10$^4$ cell/well) | Condition 3 wells | 20 60 | 1.6 × 10$^6$ 4.8 × 10$^6$ | |
| PCR | 6 well plate | Condition for drug | 22 | 1.76 × 10$^6$ | |
| | | Condition for ultrasound 3 wells | 20 126 | 1.6 × 10$^6$ 1 × 10$^7$ | |

First, to explain the material, a cell culture is comprised of human hair outer root sheath cells (HHORSC), a mesenchymal stem cell medium (MSCM), an FBS 0.25% trypsin/EDTA solution, a trypsin neutralization solution, a Dulbecco's phosphate-buffered saline (DPBS), and poly-L-lysine.

And a WST-1 cell proliferation assay system is used for WST-1 assay. Further, Trizol, a sensiFAST probe Hi-ROX one step kit, PrimeTime qPCR assay are used for PCR.

First, for culture dish coating (based on a T75 flask), 10 mL of deionized water (D.W.) is put into the T75 flask and then 15 μL of poly-L-lysine (10 mg/mL) is put into the T75 flask. Then, the T75 flask is placed in an incubator at 37° C. and an inside of the T75 flask is coated with poly-L-lysine for 1 hour. And the T75 flask is washed twice with D.W.

And a whole medium is created by using MSCM consisting of 500 mL basal medium, 25 mL FBS, and 5 mL of mesenchymal stem cells.

And, a frozen cell vial is warmed in a water bath at 37° C. Then the melted cells are placed on a growth medium of 3 mL and centrifuged at 3,000 rpm for 3 minutes to pull the cells down to the bottom. Then, DPBS is added to the centrifuged cells, and after washing, centrifuged again at 3,000 rpm for 3 minutes to pull the cells down, and these processes are repeated twice, creating cell pellets. Then, 8 mL of the growth medium is put into the T75 flask coated with poly-L-lysine, the cell pellets are dissolved therein, and after seeding, the T75 flask is placed in an incubator at 37° C. with 5% $CO_2$.

And, if it is confirmed under the microscope that the cells have grown more than 90% in the cell subculture of the T75 flask, (i) 3 mL of DPBS is added to the cell subculture and washed and (ii) 3 mL of the trypsin/EDTA solution is added and the T75 flask is placed in the incubator at 37° C. for 3 minutes. Then, if it is confirmed that the cells have fallen from the T75 flask, (i) each 3 mL of the growth medium and the trypsin neutralization solution is added to the T75 flask in order to neutralize the trypsin/EDTA solution, (ii) the neutralized cell solution is transferred to a conical tube, and centrifuged at 3,000 rpm for 3 minutes to pull the cells down, creating cell pellets, (iii) 8 mL of the growth medium is put into the T75 flask coated with poly-L-lysine, (iv) the cell pellets are dissolved in the T75 flask, and (v) after seeding, the T75 flask is placed in the incubator at 37° C. with 5% $CO_2$.

And, for 6 well plate/96 well plate cell seeding, poly-L-lysine is added for each plate according to a Table 4 below, and poly-L-lysine coating is performed according to a culture dish coating procedure.

TABLE 4

| | Required amount of poly-L-lysine per surface area (μg/cm$^2$) | | |
|---|---|---|---|
| Dish | Surface area (cm$^2$) | Required amount of poly-L-lysine (μg) | 2 Poly-L-lysine (μL) of 10 mg/mL |
| T75 | 75 | 150 | 15 |
| 100 mm | 55 | 110 | 11 |
| 6 wells | 4.8 | 9.6 | 2 |
| 12 wells | 3.9 | 7.8 | 0.78 (7.8 μL as a result of 1/10 dilution) |

TABLE 4-continued

| | Required amount of poly-L-lysine per surface area (μg/cm$^2$) | | |
|---|---|---|---|
| Dish | Surface area (cm$^2$) | Required amount of poly-L-lysine (μg) | 2 Poly-L-lysine (μL) of 10 mg/mL |
| 96 wells | 0.3 | 0.6 | 0.06 (6 μL as a result of 1/100 dilution) |

Herein, if it is confirmed under the microscope that the cells have grown more than 90% in the cell subculture of the T75 flask, (i) 3 mL of DPBS is added to the cell subculture and washed and (ii) 3 mL of the trypsin/EDTA solution is added and the T75 flask is placed in the incubator at 37° C. for 3 minutes. Then, if it is confirmed that the cells have fallen from the T75 flask, (i) each 3 mL of the growth medium and the trypsin neutralization solution is added to the T75 flask in order to neutralize the trypsin/EDTA solution, (ii) the neutralized cell solution is transferred to the conical tube, and centrifuged at 3,000 rpm for 3 minutes to pull the cells down, and (iii) the cells are counted using trypan blue and a hemocytometer. And the cells are seeded as many as $8 \times 10^4$ in the 6 well plate and $4 \times 10^4$ in the 96 well plate.

For WST assay, in a case of an experiment of the ultrasound irradiation only, the cells seeded in the 6 well plate are cultured for 12 to 18 hours and observed with the microscope. And after removing the medium, the cells are washed twice with DPBS, put into a growth factor free medium, and irradiated with the ultrasound for 10 minutes. Then, the 6 well plate is placed in the incubator at 37° C. with 5% $CO_2$ and incubated for 24 hours, then the medium is removed therefrom. The 6 well plate is then washed with DPBS, treated with 0.2 mL of WST-1, and placed in the incubator for 3 hours. Then supernatant is transferred from each well of the 6 well plate into 3 wells of a 96 well plate, and the 96 well plate is measured with a microplate reader at 450 nm.

For the WST assay, in a case of an experiment with drugs only, the cells seeded in the 96 well plate are cultured for 12 to 18 hours and confirmed whether the cells are seeded sufficiently. And after removing the medium, the cells are washed twice with DPBS, put into the growth factor free medium, and a drug is applied to the cells. Then, the 96 well plate is placed in the incubator at 37° C. with 5% $CO_2$ for 24 hours, then the medium is removed therefrom. The 96 well plate is then washed with DPBS, treated with 0.2 mL of WST-1, and placed in the incubator for 3 hours. Then the 96 well plate is measured with the microplate reader at 450 nm.

Figure 3A:
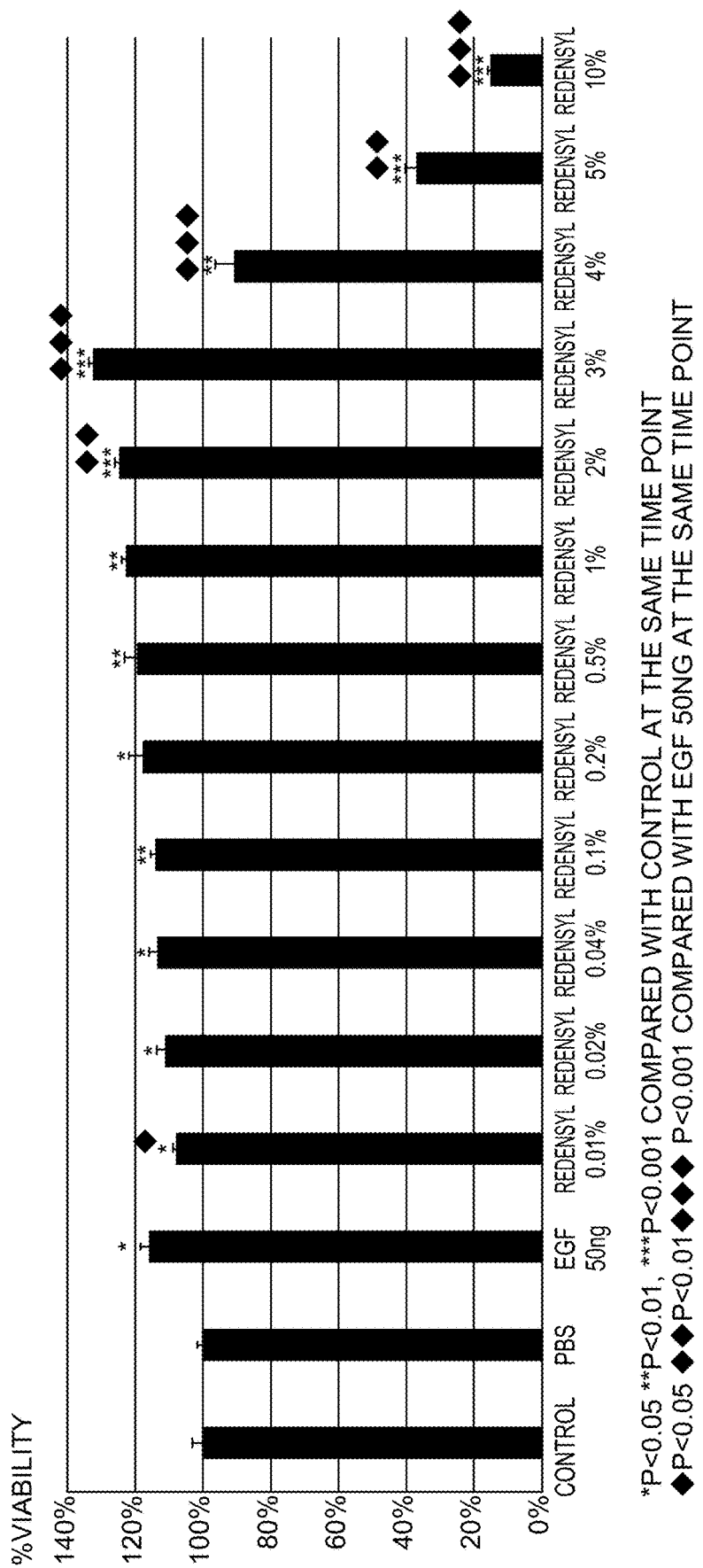
FIGS. 3A and 3B are drawings schematically illustrating the viability of human outer root sheath cells according to concentrations of applied conventional drugs in case only the conventional drugs are applied.
Figure 3B:
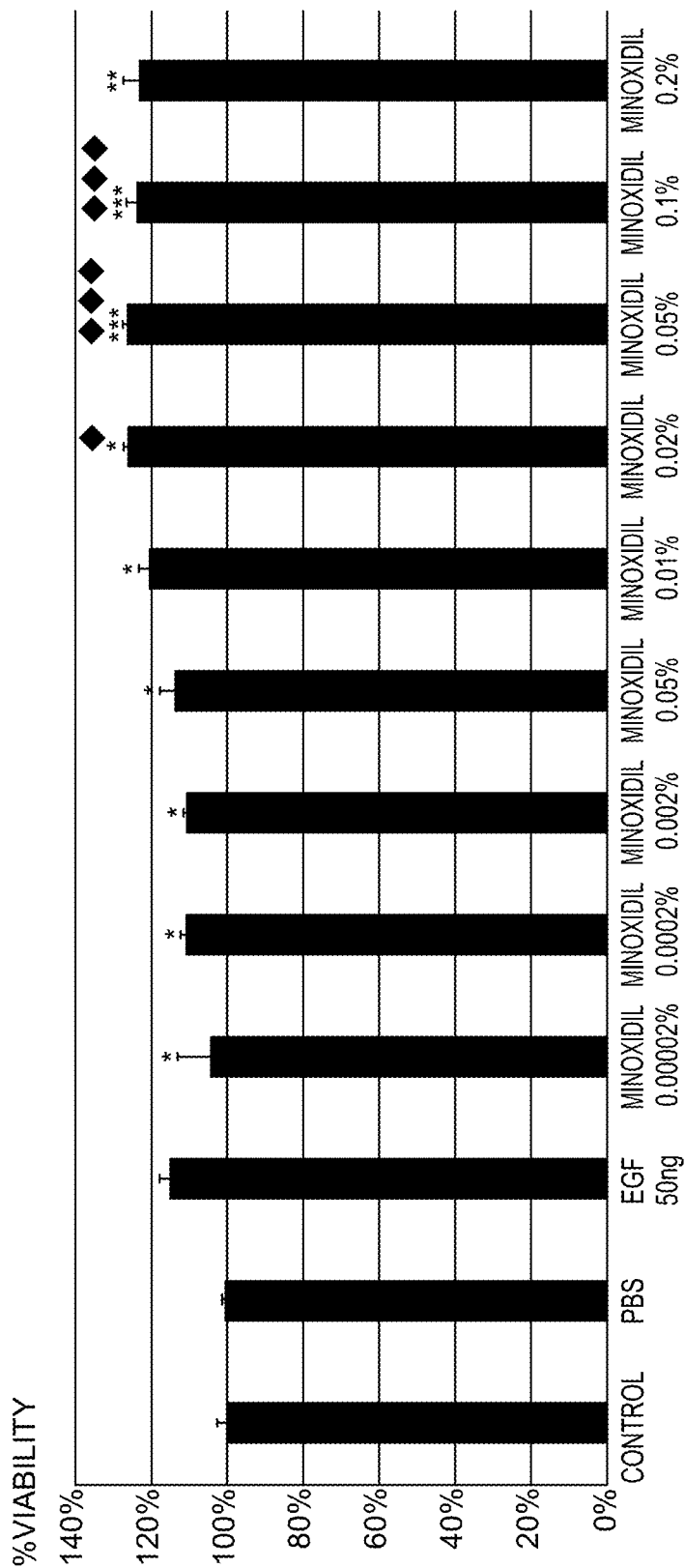

Meanwhile, FIGS. 3A and 3B are drawings schematically illustrating the viability of the human outer root sheath cells according to concentrations of applied conventional drugs in case only the conventional drugs are applied.

Specifically, FIG. 3A shows the viability of the cells according to the concentrations of applied Redensyl, i.e., a hair loss treatment drug, and FIG. 3B shows the viability of the cells according to the concentrations of applied minoxidil, i.e., another hair loss treatment drug.

For reference, a Table 5 below shows experimental conditions where the drug, the epidermal drug carrier, and the ultrasound are applied together. Herein, a solubility of minoxidil is 0.2% in PBS, on a condition of being measured 24 hours after application of the drug. For reference, blanks in the Table 5 represent that a control group, where only the ultrasound is used, is unavailable due to cell deformation caused by too strong an ultrasound.

TABLE 5

| | 96 well plate | | | 6 well plate | | | |
|---|---|---|---|---|---|---|---|
| | Positive control | | | | Ultrasound + epidermal drug carrier + Redensyl | | |
| Control | (EGF) | Minoxidil | Redensyl | Ultrasound | Ultrasound | Microbubble | Redensyl |
| Medium | 50 ng/ 100 μL | 0.00002% | 0.01% | 0.3 MPa 1% | 0.5 MPa 2% | 1:1000 | 0.04% 0.1% 0.2% |
| | | 0.0002% | 0.02% | | | | 0.5% 1% |
| | | 0.002% | 0.04% | | | | 2% 3% |
| | | 0.005% | 0.1% | 0.5 MPa 2% | 0.5 MPa 5% | | 0.04% 0.1% 0.2% |
| | | 0.01% | 0.2% | | | | 0.5% 1% |
| | | 0.02% | 0.5% | | | | 2% 3% |
| | | 0.05% | 1% | 1 MPa 2% | 1 MPa 1% | | 0.04% 0.1% 0.2% |
| | | 0.15% | 2% | | | | 0.5% 1% |
| | | 0.2% | 3% | | | | 2% 3% |
| | | | 4% | | 1 MPa 3% | | 0.04% 0.1% 0.2% |
| | | | 5% | | | | 0.5% 1% |
| | | | 10% | | | | 2% 3% |

Figure 4:
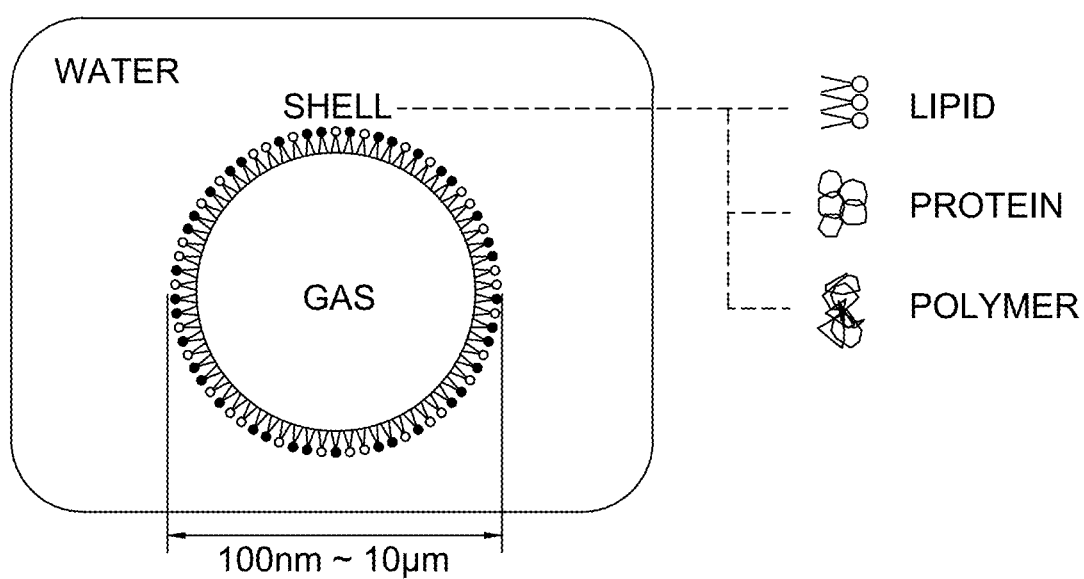
FIG. 4 is a drawing schematically illustrating an epidermal drug carrier used in the method for increasing the viability of the cells by irradiating the cells with the ultrasound in accordance with one example embodiment of the present disclosure.

Next, FIG. 4 is a drawing schematically illustrating the epidermal drug carrier in accordance with one example embodiment of the present disclosure.

As an example, the epidermal drug carrier may be configured with a single membrane as shown in FIG. 4, but the scope of the present disclosure is not limited thereto, and may be formed of a plurality of membranes such as an outer membrane and an inner membrane, etc., or may have a structure incorporating a drug inside the membrane.

Meanwhile, in the cell experiment, a comparison between MTT and WST-1 was performed, and in the case of MTT, there was a problem of overlapping between an absorbance range of Redensyl and an absorbance range of MTT, resulting in a poor data accuracy. On the other hand, in the case of WST-1, since the absorbance range of Redensyl and the absorbance range of WST-1 did not overlap each other, the experiment was conducted by using WST-1.

In addition, a media comparison was performed. In a first experiment, after seeding stabilization, complete media was treated with Redensyl and observed for 24 hours. However, a time duration is not limited to 24 hours, and may be changed according to cell conditions. Also, in a second experiment, after the seeding stabilization, the media without a growth factor were treated with Redensyl and observed for 24 hours. Like the first experiment, the time duration of the second experiment may be changed according to the cell conditions.

By referring to the first experiment and the second experiment, an effect of the ultrasound was better observed when the media did not contain the growth factor. Therefore, the experiment was conducted by treating the media, which did not contain the growth factor, with Redensyl.

Subsequently, the ultrasound irradiation was conducted, and a quantitative analysis was performed through an assay before and after the ultrasound irradiation.

Tables 6 to 9 describe the experimental conditions of the ultrasound irradiation for evaluating physical effects of the ultrasound on the cells.

Specifically, Tables 6 and 7 describe observation conditions of Redensyl treatment on serum free media and complete media left overnight during the stabilization after the seeding.

TABLE 6

| 96Well-1 | A | B | C | D | E | F | G | H |
|---|---|---|---|---|---|---|---|---|
| 1 | M-24-XTT | M-24-XTT | M-24-XTT | M-24-XTT | M-24-XTT | M-24-XTT | M-24-XTT | M-24-XTT |
| 2 | P-24-XTT | P-24-XTT | P-24-XTT | P-24-XTT | P-24-XTT | P-24-XTT | P-24-XTT | P-24-XTT |
| 3 | R0.01-24-XTT | R0.01-24-XTT | R0.01-24-XTT | R0.01-24-XTT | R0.01-24-XTT | R0.01-24-XTT | R0.01-24-XTT | R0.01-24-XTT |
| 4 | R0.04-24-XTT | R0.04-24-XTT | R0.04-24-XTT | R0.04-24-XTT | R0.04-24-XTT | R0.04-24-XTT | R0.04-24-XTT | R0.04-24-XTT |
| 5 | R0.2-24-XTT | R0.2-24-XTT | R0.2-24-XTT | R0.2-24-XTT | R0.2-24-XTT | R0.2-24-XTT | R0.2-24-XTT | R0.2-24-XTT |
| 6 | R1-24-XTT | R1-24-XTT | R1-24-XTT | R1-24-XTT | R1-24-XTT | R1-24-XTT | R1-24-XTT | R1-24-XTT |

TABLE 6-continued

| 96Well-1 | A | B | C | D | E | F | G | H |
|---|---|---|---|---|---|---|---|---|
| 7 | M-24-WST | M-24-WST | M-24-WST | M-24-WST | M-24-WST | M-24-WST | M-24-WST | M-24-WST |
| 8 | P-24-WST | P-24-WST | P-24-WST | P-24-WST | P-24-WST | P-24-WST | P-24-WST | P-24-WST |
| 9 | R0.01-24-WST | R0.01-24-WST | R0.01-24-WST | R0.01-24-WST | R0.01-24-WST | R0.01-24-WST | R0.01-24-WST | R0.01-24-WST |
| 10 | R0.04-24-WST | R0.04-24-WST | R0.04-24-WST | R0.04-24-WST | R0.04-24-WST | R0.04-24-WST | R0.04-24-WST | R0.04-24-WST |
| 11 | R0.2-24-WST | R0.2-24-WST | R0.2-24-WST | R0.2-24-WST | R0.2-24-WST | R0.2-24-WST | R0.2-24-WST | R0.2-24-WST |
| 12 | R1-24-WST | R1-24-WST | R1-24-WST | R1-24-WST | R1-24-WST | R1-24-WST | R1-24-WST | R1-24-WST |

TABLE 7

| 96Well-2 | A | B | C | D | E | F | G | H |
|---|---|---|---|---|---|---|---|---|
| 1 | M-48-XTT | M-48-XTT | M-48-XTT | M-48-XTT | M-48-XTT | M-48-XTT | M-48-XTT | M-48-XTT |
| 2 | P-48-XTT | P-48-XTT | P-48-XTT | P-48-XTT | P-48-XTT | P-48-XTT | P-48-XTT | P-48-XTT |
| 3 | R0.01-48-XTT | R0.01-48-XTT | R0.01-48-XTT | R0.01-48-XTT | R0.01-48-XTT | R0.01-48-XTT | R0.01-48-XTT | R0.01-48-XTT |
| 4 | R0.04-48-XTT | R0.04-48-XTT | R0.04-48-XTT | R0.04-48-XTT | R0.04-48-XTT | R0.04-48-XTT | R0.04-48-XTT | R0.04-48-XTT |
| 5 | R0.2-48-XTT | R0.2-48-XTT | R0.2-48-XTT | R0.2-48-XTT | R0.2-48-XTT | R0.2-48-XTT | R0.2-48-XTT | R0.2-48-XTT |
| 6 | R1-48-XTT | R1-48-XTT | R1-48-XTT | R1-48-XTT | R1-48-XTT | R1-48-XTT | R1-48-XTT | R1-48-XTT |
| 7 | M-48-WST | M-48-WST | M-48-WST | M-48-WST | M-48-WST | M-48-WST | M-48-WST | M-48-WST |
| 8 | P-48-WST | P-48-WST | P-48-WST | P-48-WST | P-48-WST | P-48-WST | P-48-WST | P-48-WST |
| 9 | R0.01-48-WST | R0.01-48-WST | R0.01-48-WST | R0.01-48-WST | R0.01-48-WST | R0.01-48-WST | R0.01-48-WST | R0.01-48-WST |
| 10 | R0.04-48-WST | R0.04-48-WST | R0.04-48-WST | R0.04-48-WST | R0.04-48-WST | R0.04-48-WST | R0.04-48-WST | R0.04-48-WST |
| 11 | R0.2-48-WST | R0.2-48-WST | R0.2-48-WST | R0.2-48-WST | R0.2-48-WST | R0.2-48-WST | R0.2-48-WST | R0.2-48-WST |
| 12 | R1-48-WST | R1-48-WST | R1-48-WST | R1-48-WST | R1-48-WST | R1-48-WST | R1-48-WST | R1-48-WST |

In addition, Tables 8 and 9 describe the conditions of Redensyl treatment on the serum free media after the seeding and the stabilization.

TABLE 8

| 96Well-3 | A | B | C | D | E | F | G | H |
|---|---|---|---|---|---|---|---|---|
| 1 | M-24-XTT | M-24-XTT | M-24-XTT | M-24-XTT | M-24-XTT | M-24-XTT | M-24-XTT | M-24-XTT |
| 2 | P-24-XTT | P-24-XTT | P-24-XTT | P-24-XTT | P-24-XTT | P-24-XTT | P-24-XTT | P-24-XTT |
| 3 | R0.01-24-XTT | R0.01-24-XTT | R0.01-24-XTT | R0.01-24-XTT | R0.01-24-XTT | R0.01-24-XTT | R0.01-24-XTT | R0.01-24-XTT |
| 4 | R0.04-24-XTT | R0.04-24-XTT | R0.04-24-XTT | R0.04-24-XTT | R0.04-24-XTT | R0.04-24-XTT | R0.04-24-XTT | R0.04-24-XTT |
| 5 | R0.2-24-XTT | R0.2-24-XTT | R0.2-24-XTT | R0.2-24-XTT | R0.2-24-XTT | R0.2-24-XTT | R0.2-24-XTT | R0.2-24-XTT |
| 6 | R1-24-XTT | R1-24-XTT | R1-24-XTT | R1-24-XTT | R1-24-XTT | R1-24-XTT | R1-24-XTT | R1-24-XTT |
| 7 | M-24-WST | M-24-WST | M-24-WST | M-24-WST | M-24-WST | M-24-WST | M-24-WST | M-24-WST |
| 8 | P-24-WST | P-24-WST | P-24-WST | P-24-WST | P-24-WST | P-24-WST | P-24-WST | P-24-WST |
| 9 | R0.01-24-WST | R0.01-24-WST | R0.01-24-WST | R0.01-24-WST | R0.01-24-WST | R0.01-24-WST | R0.01-24-WST | R0.01-24-WST |
| 10 | R0.04-24-WST | R0.04-24-WST | R0.04-24-WST | R0.04-24-WST | R0.04-24-WST | R0.04-24-WST | R0.04-24-WST | R0.04-24-WST |
| 11 | R0.2-24-WST | R0.2-24-WST | R0.2-24-WST | R0.2-24-WST | R0.2-24-WST | R0.2-24-WST | R0.2-24-WST | R0.2-24-WST |

TABLE 8-continued

| 96Well-3 | A | B | C | D | E | F | G | H |
|---|---|---|---|---|---|---|---|---|
| 12 | R1-24-WST | R1-24-WST | R1-24-WST | R1-24-WST | R1-24-WST | R1-24-WST | R1-24-WST | R1-24-WST |

TABLE 9

| 96Well-4 | A | B | C | D | E | F | G | H |
|---|---|---|---|---|---|---|---|---|
| 1 | M-48-XTT | M-48-XTT | M-48-XTT | M-48-XTT | M-48-XTT | M-48-XTT | M-48-XTT | M-48-XTT |
| 2 | P-48-XTT | P-48-XTT | P-48-XTT | P-48-XTT | P-48-XTT | P-48-XTT | P-48-XTT | P-48-XTT |
| 3 | R0.01-48-XTT | R0.01-48-XTT | R0.01-48-XTT | R0.01-48-XTT | R0.01-48-XTT | R0.01-48-XTT | R0.01-48-XTT | R0.01-48-XTT |
| 4 | R0.04-48-XTT | R0.04-48-XTT | R0.04-48-XTT | R0.04-48-XTT | R0.04-48-XTT | R0.04-48-XTT | R0.04-48-XTT | R0.04-48-XTT |
| 5 | R0.2-48-XTT | R0.2-48-XTT | R0.2-48-XTT | R0.2-48-XTT | R0.2-48-XTT | R0.2-48-XTT | R0.2-48-XTT | R0.2-48-XTT |
| 6 | R1-48-XTT | R1-48-XTT | R1-48-XTT | R1-48-XTT | R1-48-XTT | R1-48-XTT | R1-48-XTT | R1-48-XTT |
| 7 | M-48-WST | M-48-WST | M-48-WST | M-48-WST | M-48-WST | M-48-WST | M-48-WST | M-48-WST |
| 8 | P-48-WST | P-48-WST | P-48-WST | P-48-WST | P-48-WST | P-48-WST | P-48-WST | P-48-WST |
| 9 | R0.01-48-WST | R0.01-48-WST | R0.01-48-WST | R0.01-48-WST | R0.01-48-WST | R0.01-48-WST | R0.01-48-WST | R0.01-48-WST |
| 10 | R0.04-48-WST | R0.04-48-WST | R0.04-48-WST | R0.04-48-WST | R0.04-48-WST | R0.04-48-WST | R0.04-48-WST | R0.04-48-WST |
| 11 | R0.2-48-WST | R0.2-48-WST | R0.2-48-WST | R0.2-48-WST | R0.2-48-WST | R0.2-48-WST | R0.2-48-WST | R0.2-48-WST |
| 12 | R1-48-WST | R1-48-WST | R1-48-WST | R1-48-WST | R1-48-WST | R1-48-WST | R1-48-WST | R1-48-WST |

Also, Table 10 describes the experimental conditions for irradiating the ultrasound while varying the pressure and the duty percentage of the ultrasound.

TABLE 10

| | 1 | 2 | 3 |
|---|---|---|---|
| 6Well-1 | | | |
| A | 1 MPa, 3% | 1 MPa, 2% | 1 MPa, 1% |
| B | 0.5 MPa, 3% | 0.5 MPa, 2% | 0.5 MPa, 1% |
| 6Well-2 | | | |
| A | 1 MPa, 3% | 1 MPa, 2% | 1 MPa, 1% |
| B | 0.5 MPa, 3% | 0.5 MPa, 2% | 0.5 MPa, 1% |
| 6Well-3 | | | |
| A | 1 MPa, 3% | 1 MPa, 2% | 1 MPa, 1% |
| B | 0.5 MPa, 3% | 0.5 MPa, 2% | 0.5 MPa, 1% |
| 6Well-4 | | | |
| A | Control | Control | Control |
| B | 1.5 MPa, 10% | 1.5 MPa, 5% | |
| 6Well-5 | | | |
| A | | | |
| B | | | |
| 6Well-6 | | | |
| A | | | |
| B | | | |

By referring to the Table 10, while varying the pressure (0.5 MPa, 1 MPa, and 1.5 MPa) and the duty percentage (1%, 2%, and 3%) of the ultrasound, the experiment was performed in which the cells were irradiated with the ultrasound for 10 minutes.

Specifically, in the wells No. 1 to No. 3, the ultrasound with the pressure of 0.5 MPa or 1 MPa, and the duty percentage of 1% to 3% is used.

However, in the well No. 4, the higher pressure (1.5 MPa) and the higher duty percentage (5% and 10%) were used for inducing cell death in order to compare the results of other pressures and other duty percentages with the results thereof.

The results are shown in FIGS. 5 to 21.

Figure 5:
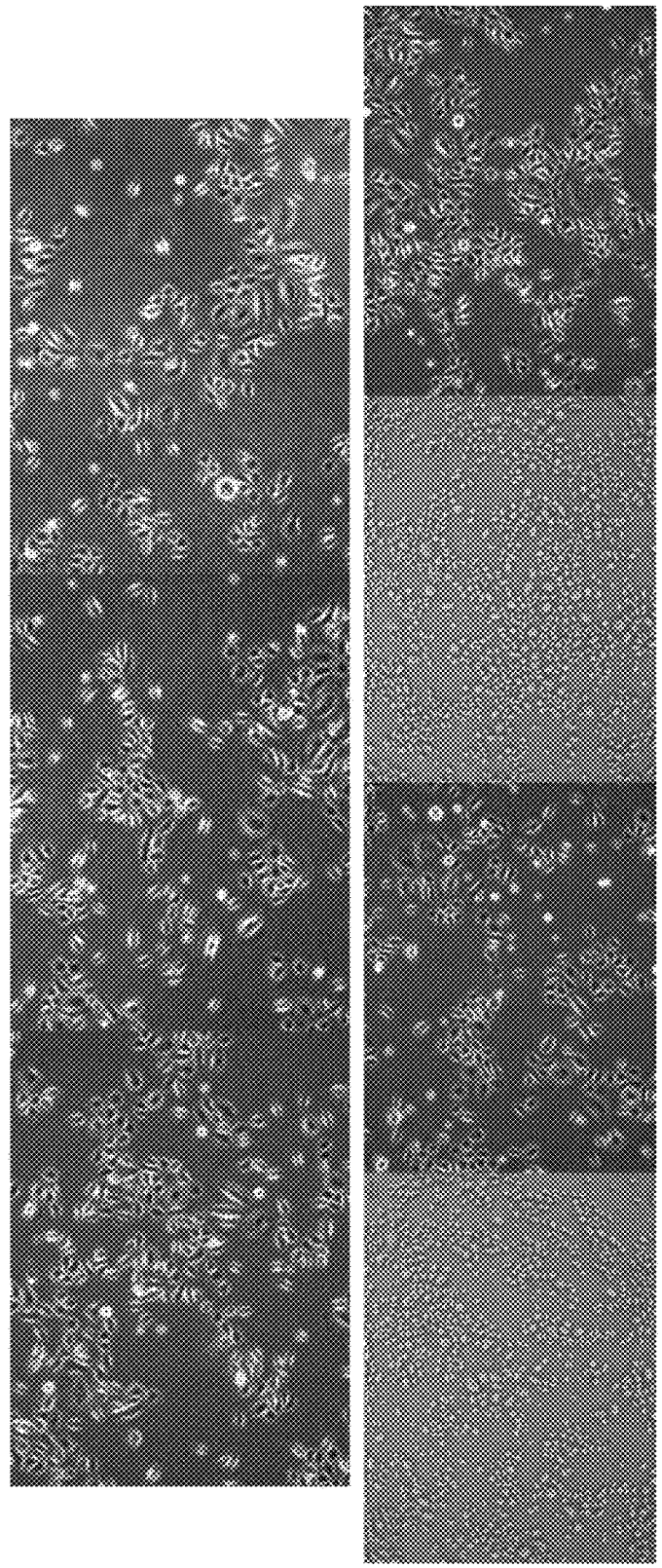
FIGS. 5 to 21 are drawings schematically illustrating physical effects of the ultrasound while varying the ultrasound parameters in accordance with one example embodiment of the present disclosure.

First, FIG. 5 shows the viability of the human outer root sheath cells at a specific point of time and the viability of the human outer root sheath cells after 12 hours from the specific point of time, wherein the human outer root sheath cells are not irradiated with the ultrasound, serving as the control group to be used for comparison with an experiment group with which the ultrasound is irradiated.

By referring to FIG. 5, if the human outer root sheath cells are not irradiated with the ultrasound then no significant changes are observed in the viability after 12 hours from the specific point of time represented in drawings shown on a right side, compared to the viability at the specific point of time represented in drawings shown on a left side.

Figure 6:
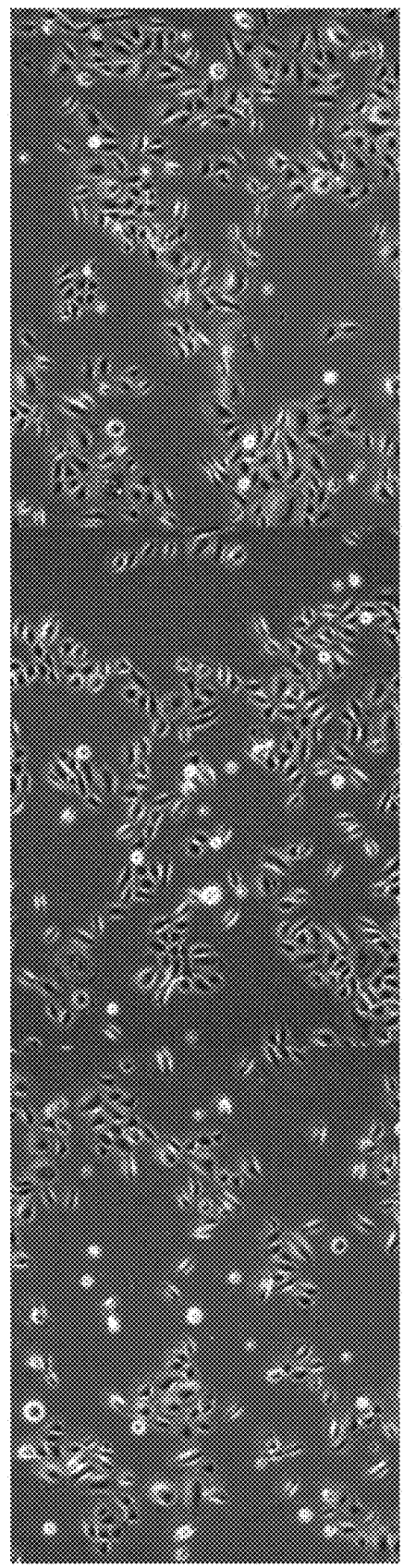

FIG. 6 is a drawing schematically illustrating experimental results right after the human outer root sheath cells are irradiated with the ultrasound (the pressure: 0.5 MPa and the duty percentage: 1%) in accordance with one example embodiment of the present disclosure.

Figure 7:
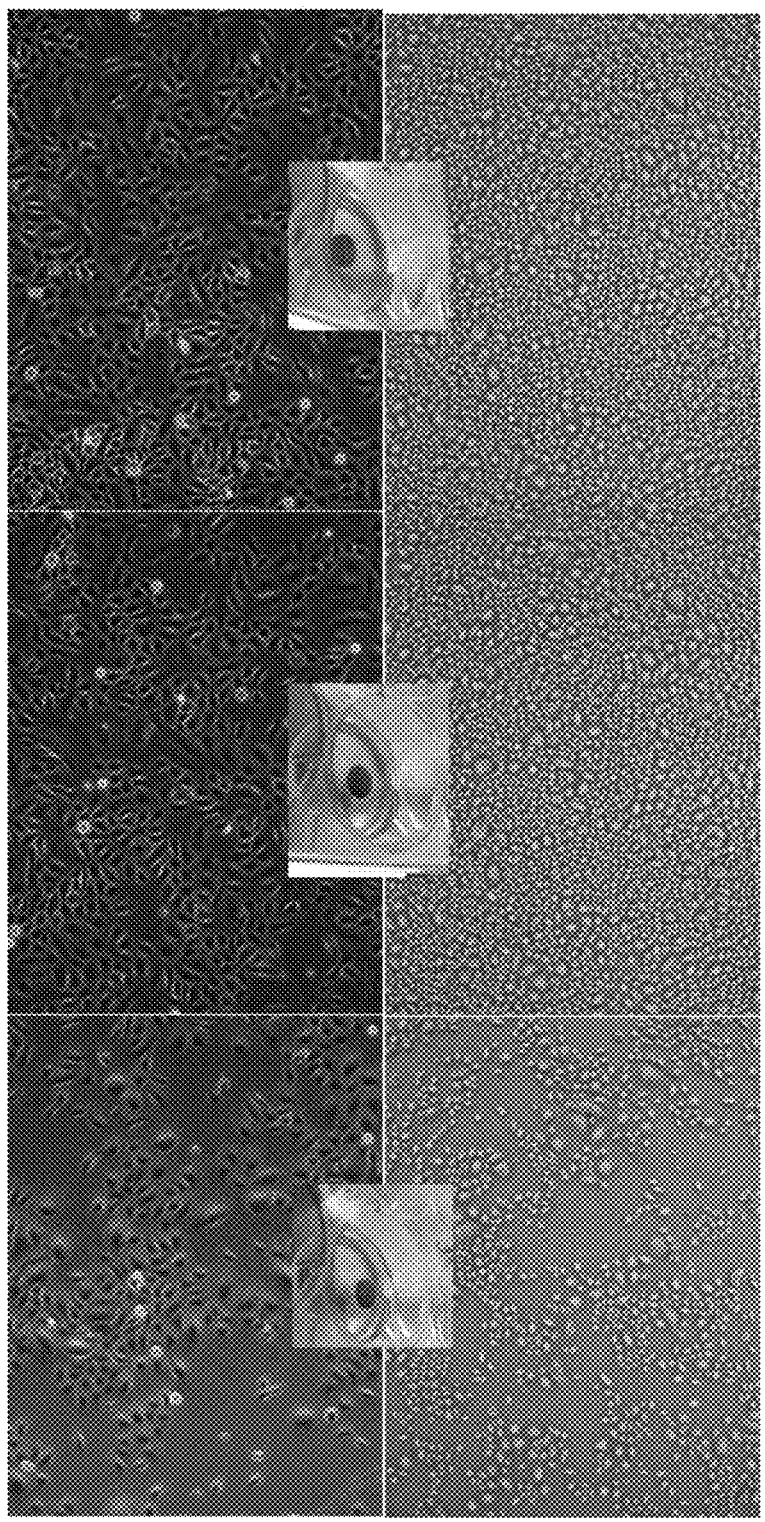

FIG. 7 is a drawing schematically illustrating experimental results 12 hours after the human outer root sheath cells are irradiated with the ultrasound (the pressure: 0.5 MPa and the duty percentage: 1%) in accordance with one example embodiment of the present disclosure.

By referring to FIGS. 6 and 7, compared to the results of the control group after 12 hours, an increase is observed in the viability of the cells 12 hours after the cells are irradiated with the ultrasound (the pressure: 0.5 MPa and the duty percentage: 1%).

Figure 8:
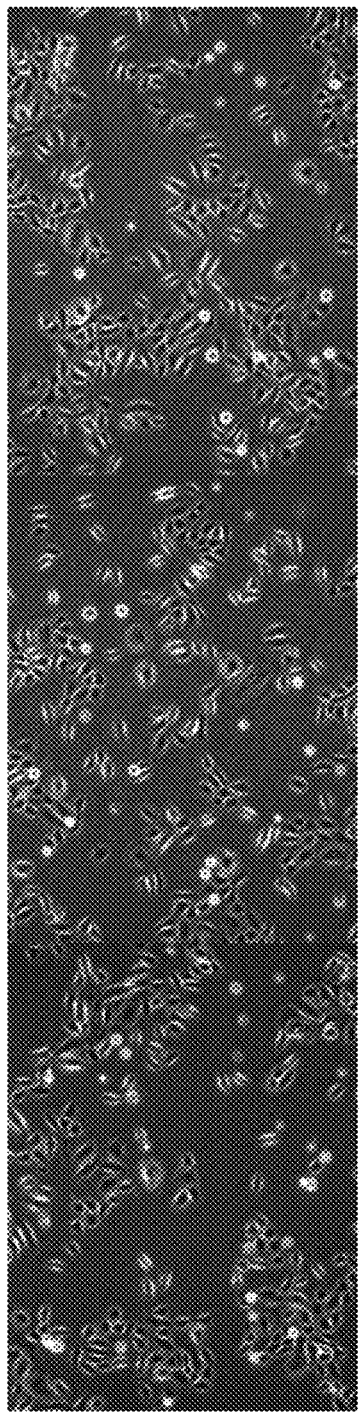

FIG. 8 is a drawing schematically illustrating experimental results right after the human outer root sheath cells are irradiated with the ultrasound (the pressure: 0.5 MPa and the duty percentage: 2%) in accordance with one example embodiment of the present disclosure.

Figure 9:
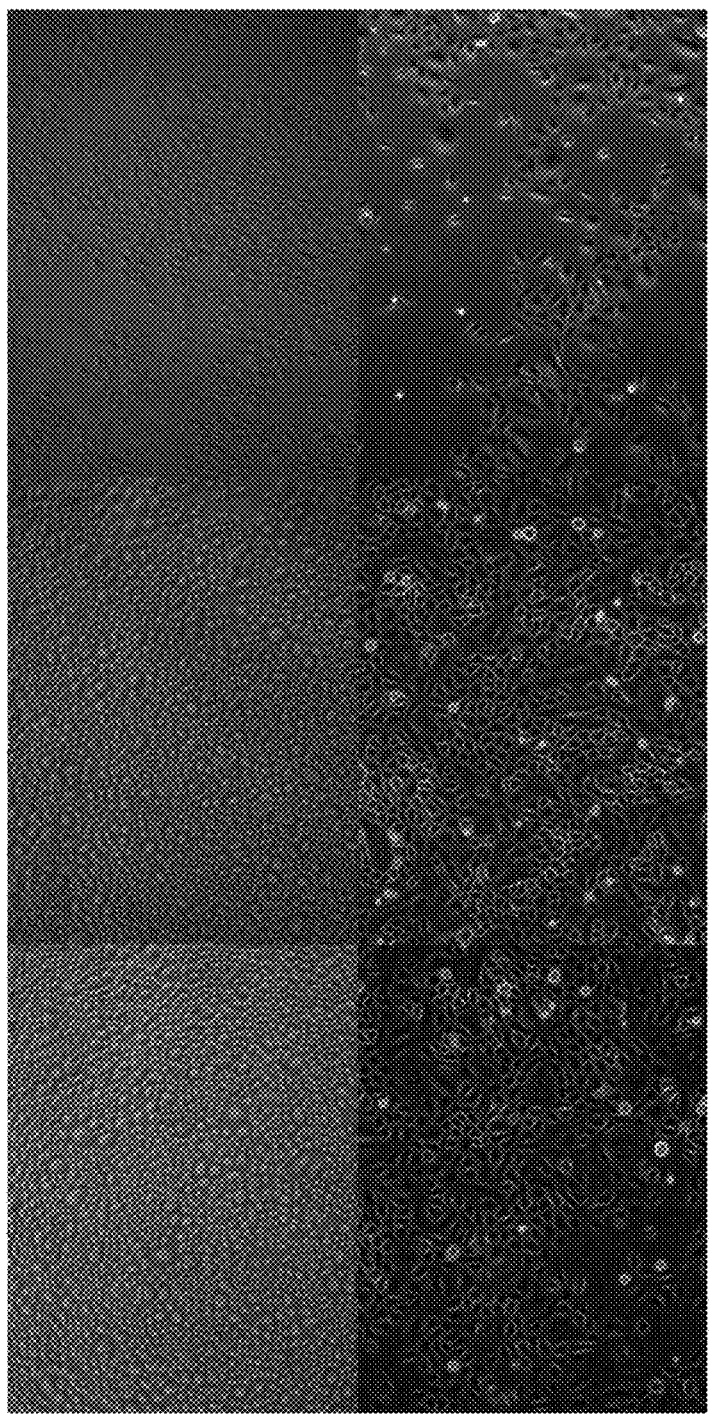

FIG. 9 is a drawing schematically illustrating experimental results 12 hours after the human outer root sheath cells are irradiated with the ultrasound (the pressure: 0.5 MPa and the duty percentage: 2%) in accordance with one example embodiment of the present disclosure.

By referring to FIGS. 8 and 9, compared to the results of the control group after 12 hours, an increase is observed in the viability of the cells 12 hours after the cells are irradiated with the ultrasound (the pressure: 0.5 MPa and the duty percentage: 2%).

Figure 10:
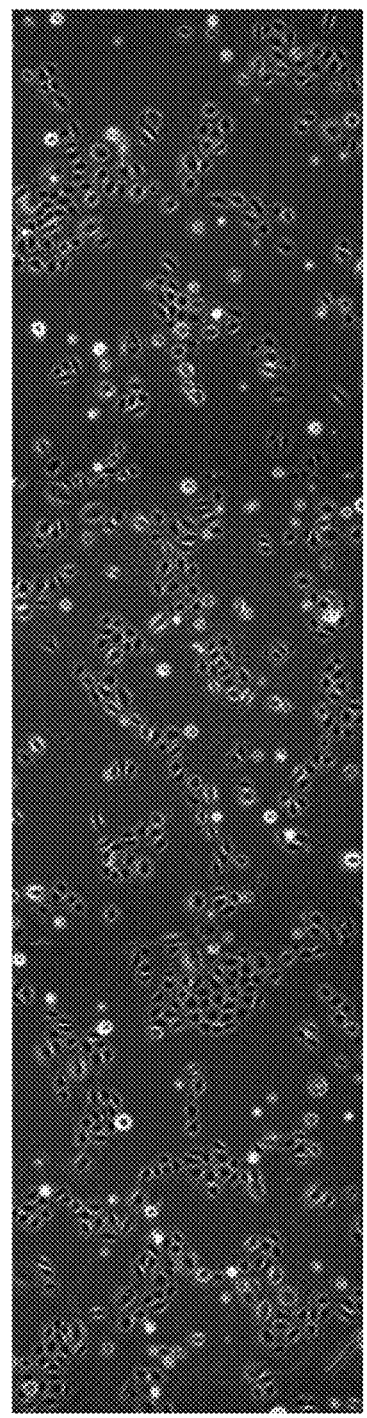

FIG. 10 is a drawing schematically illustrating experimental results right after the human outer root sheath cells are irradiated with the ultrasound (the pressure: 0.5 MPa and the duty percentage: 3%) in accordance with one example embodiment of the present disclosure.

Figure 11:
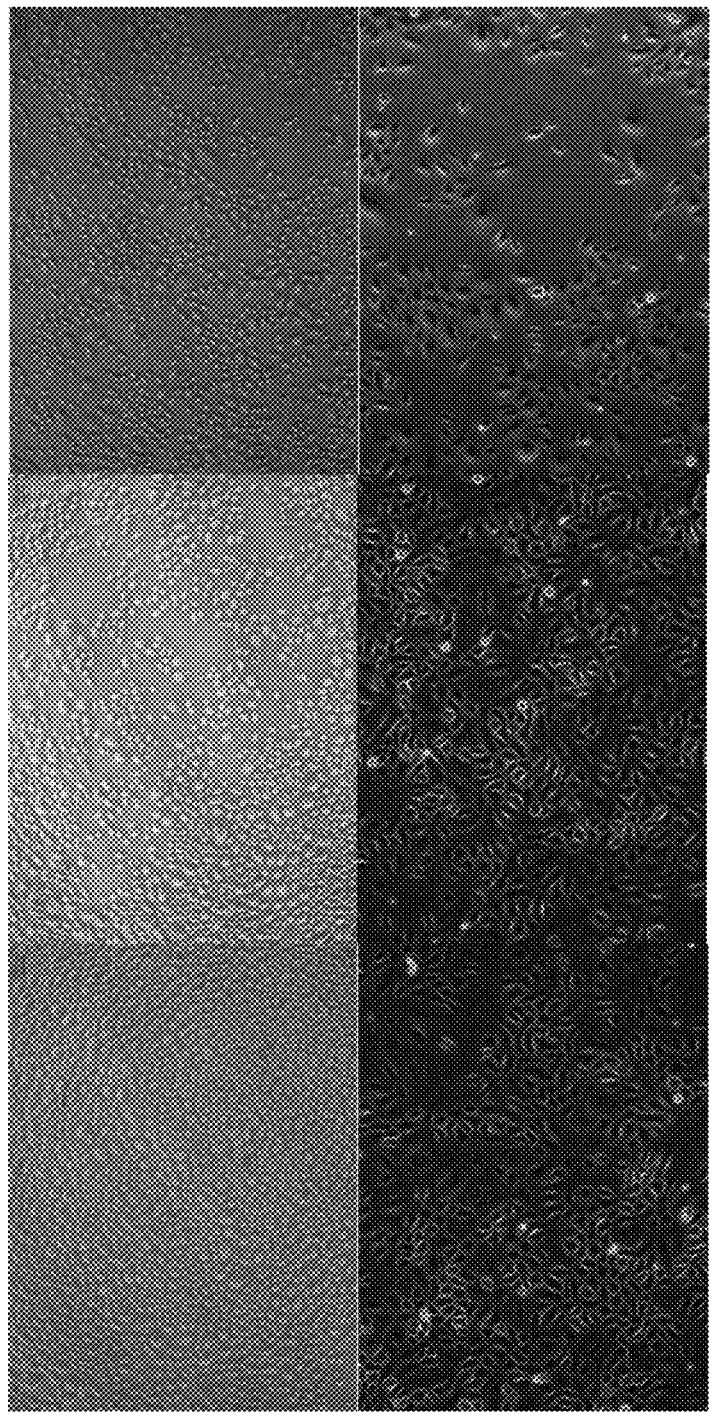

FIG. 11 is a drawing schematically illustrating experimental results 12 hours after the human outer root sheath cells are irradiated with the ultrasound (the pressure: 0.5 MPa and the duty percentage: 3%) in accordance with one example embodiment of the present disclosure.

By referring to FIGS. 10 and 11, compared to the results of the control group after 12 hours, an increase is observed in the viability of the cells 12 hours after the cells are irradiated with the ultrasound (the pressure: 0.5 MPa and the duty percentage: 3%).

Figure 12:
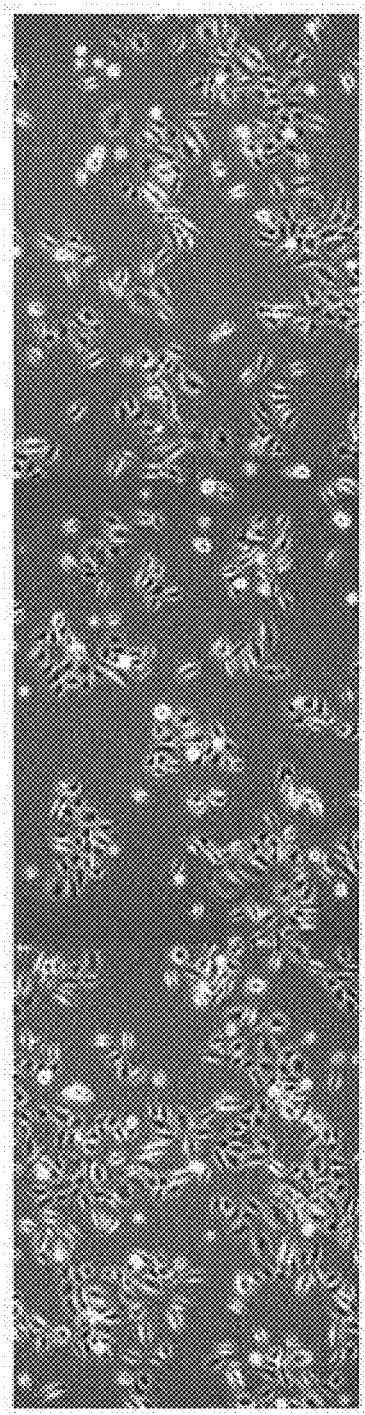

FIG. 12 is a drawing schematically illustrating experimental results right after the human outer root sheath cells are irradiated with the ultrasound (the pressure: 1 MPa and the duty percentage: 1%) in accordance with one example embodiment of the present disclosure.

Figure 13:
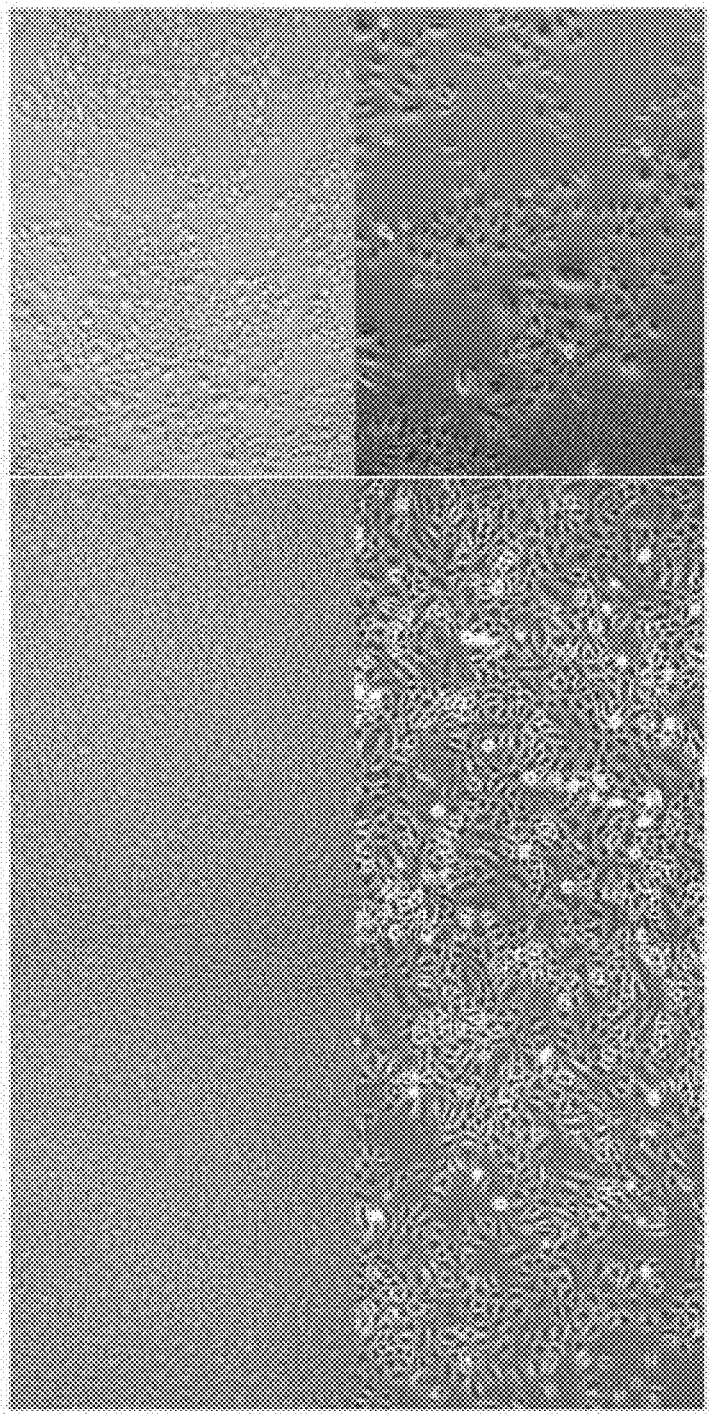

FIG. 13 is a drawing schematically illustrating experimental results 12 hours after the human outer root sheath cells are irradiated with the ultrasound (the pressure: 1 MPa and the duty percentage: 1%) in accordance with one example embodiment of the present disclosure.

By referring to FIGS. 12 and 13, compared to the results of the control group after 12 hours, an increase is observed in the viability of the cells 12 hours after the cells are irradiated with the ultrasound (the pressure: 1 MPa and the duty percentage: 1%).

Figure 14:
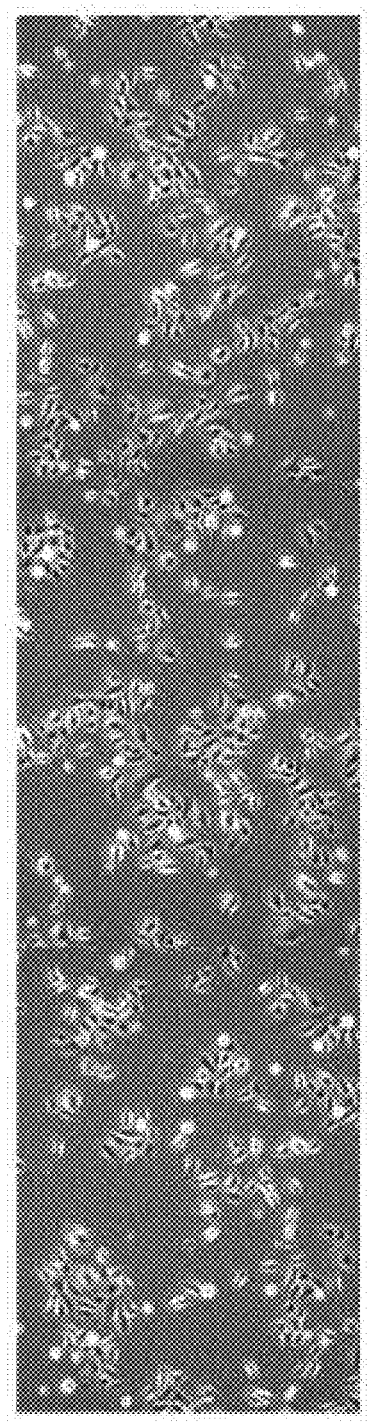

FIG. 14 is a drawing schematically illustrating experimental results right after the human outer root sheath cells are irradiated with the ultrasound (the pressure: 1 MPa and the duty percentage: 2%) in accordance with one example embodiment of the present disclosure.

Figure 15:
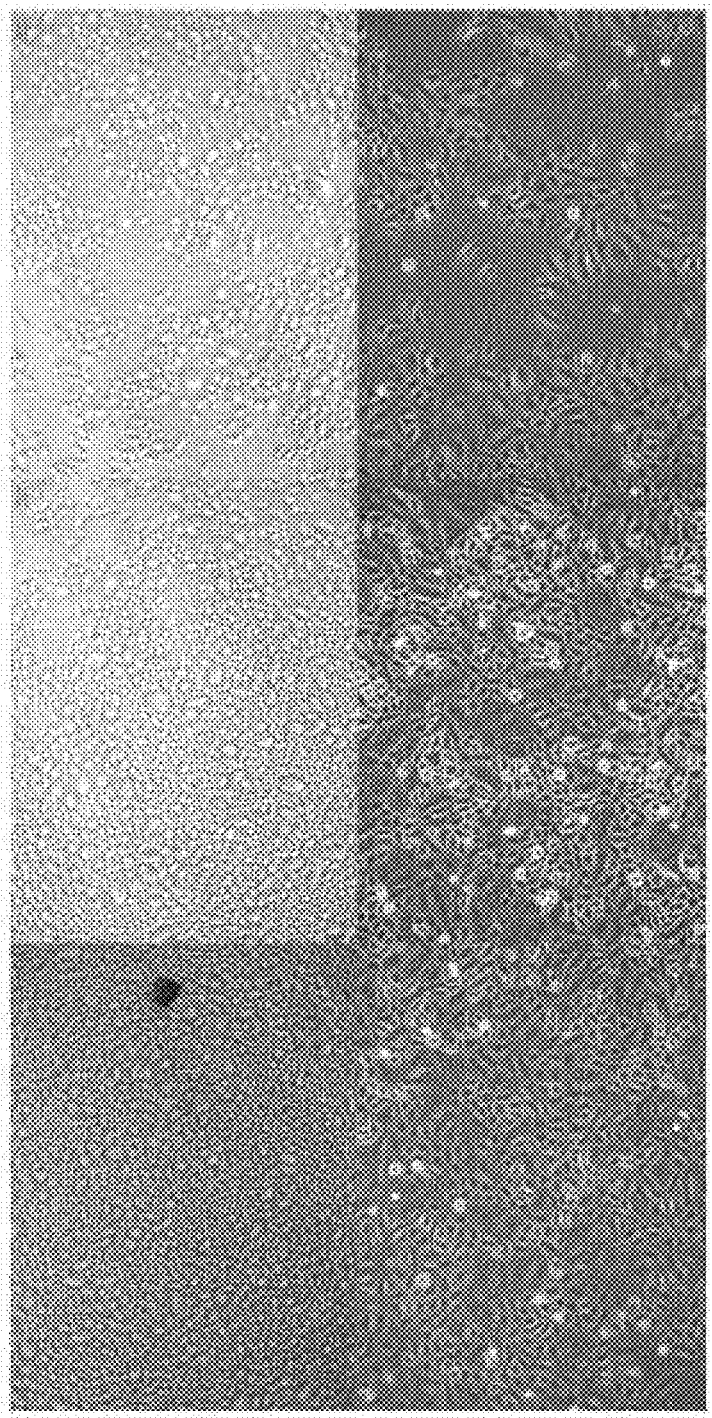

FIG. 15 is a drawing schematically illustrating experimental results 12 hours after the human outer root sheath cells are irradiated with the ultrasound (the pressure: 1 MPa and the duty percentage: 2%) in accordance with one example embodiment of the present disclosure.

By referring to FIGS. 14 and 15, compared to the results of the control group after 12 hours, a decrease is observed in the viability of the cells, for example, cell bursting or deformation, 12 hours after the cells are irradiated with the ultrasound (the pressure: 1 MPa and the duty percentage: 2%).

Figure 16:
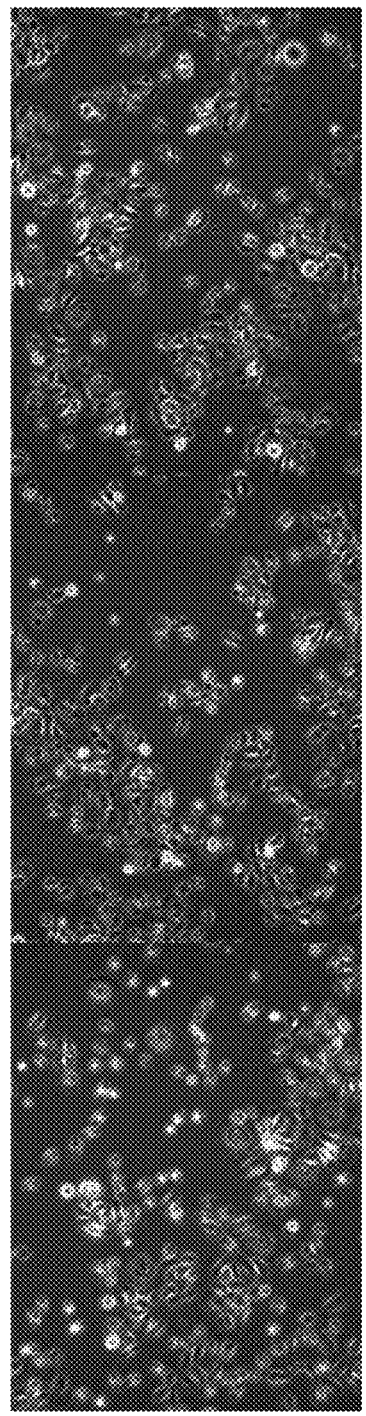

FIG. 16 is a drawing schematically illustrating experimental results right after the human outer root sheath cells are irradiated with the ultrasound (the pressure: 1 MPa and the duty percentage: 3%) in accordance with one example embodiment of the present disclosure.

Figure 17:
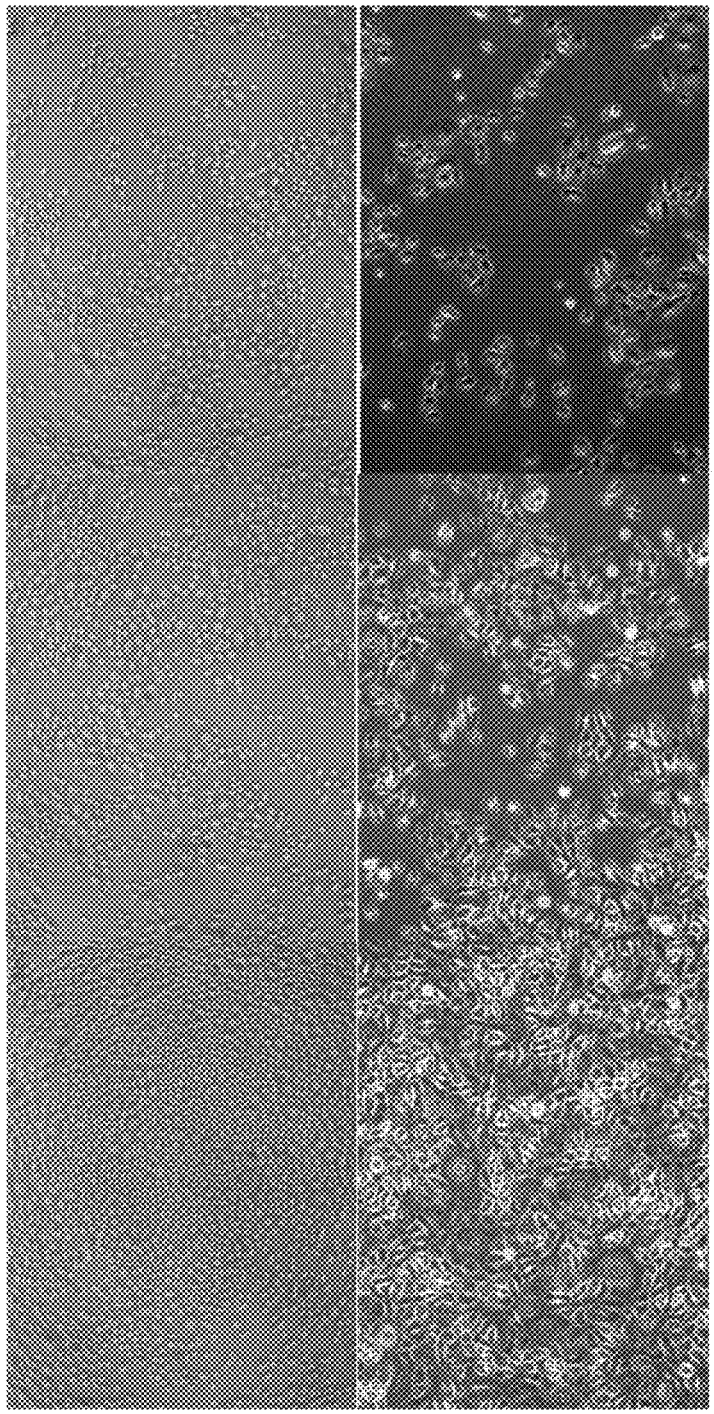

FIG. 17 is a drawing schematically illustrating experimental results 12 hours after the human outer root sheath cells are irradiated with the ultrasound (the pressure: 1 MPa and the duty percentage: 3%) in accordance with one example embodiment of the present disclosure.

By referring to FIGS. 16 and 17, compared to the results of the control group after 12 hours, a decrease is observed in the viability of the cells, for example, the cell bursting or the deformation, at the time of the ultrasound irradiation and 12 hours after the ultrasound irradiation (the pressure: 1 MPa and the duty percentage: 3%).

Figure 18:
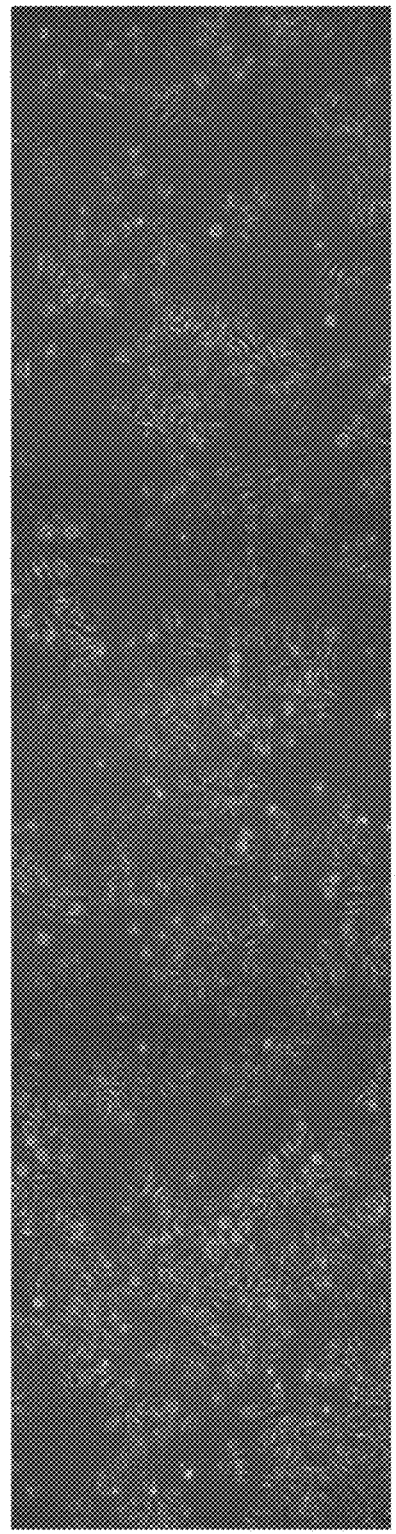

FIG. 18 is a drawing schematically illustrating experimental results right after the human outer root sheath cells are irradiated with the ultrasound (the pressure: 1.5 MPa and the duty percentage: 5%) in accordance with one example embodiment of the present disclosure.

Figure 19:
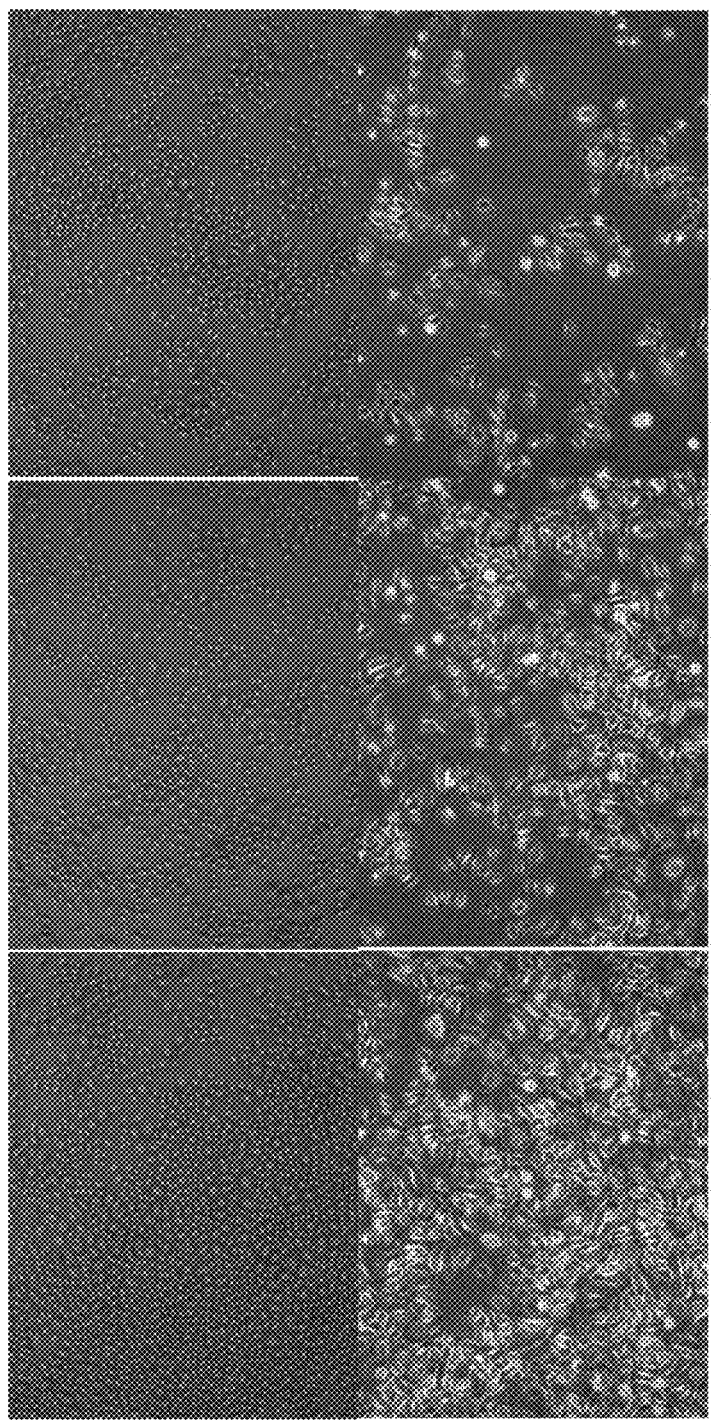

FIG. 19 is a drawing schematically illustrating experimental results 12 hours after the human outer root sheath cells are irradiated with the ultrasound (the pressure: 1.5 MPa and the duty percentage: 5%) in accordance with one example embodiment of the present disclosure.

By referring to FIGS. 18 and 19, compared to the results of the control group after 12 hours, a decrease is observed in the viability of the cells, for example, the cell bursting or the deformation with a high ratio, at the time of the ultrasound irradiation and 12 hours after the ultrasound irradiation (the pressure: 1.5 MPa and the duty percentage: 5%).

Figure 20:
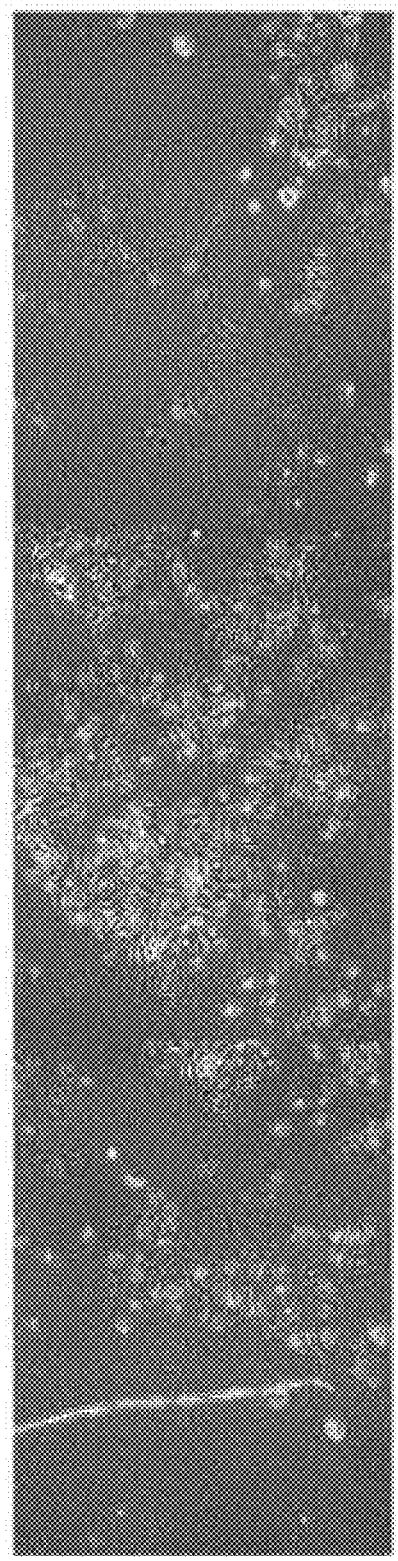

FIG. 20 is a drawing schematically illustrating experimental results right after the human outer root sheath cells are irradiated with the ultrasound (the pressure: 1.5 MPa and the duty percentage: 10%) in accordance with one example embodiment of the present disclosure.

Figure 21:
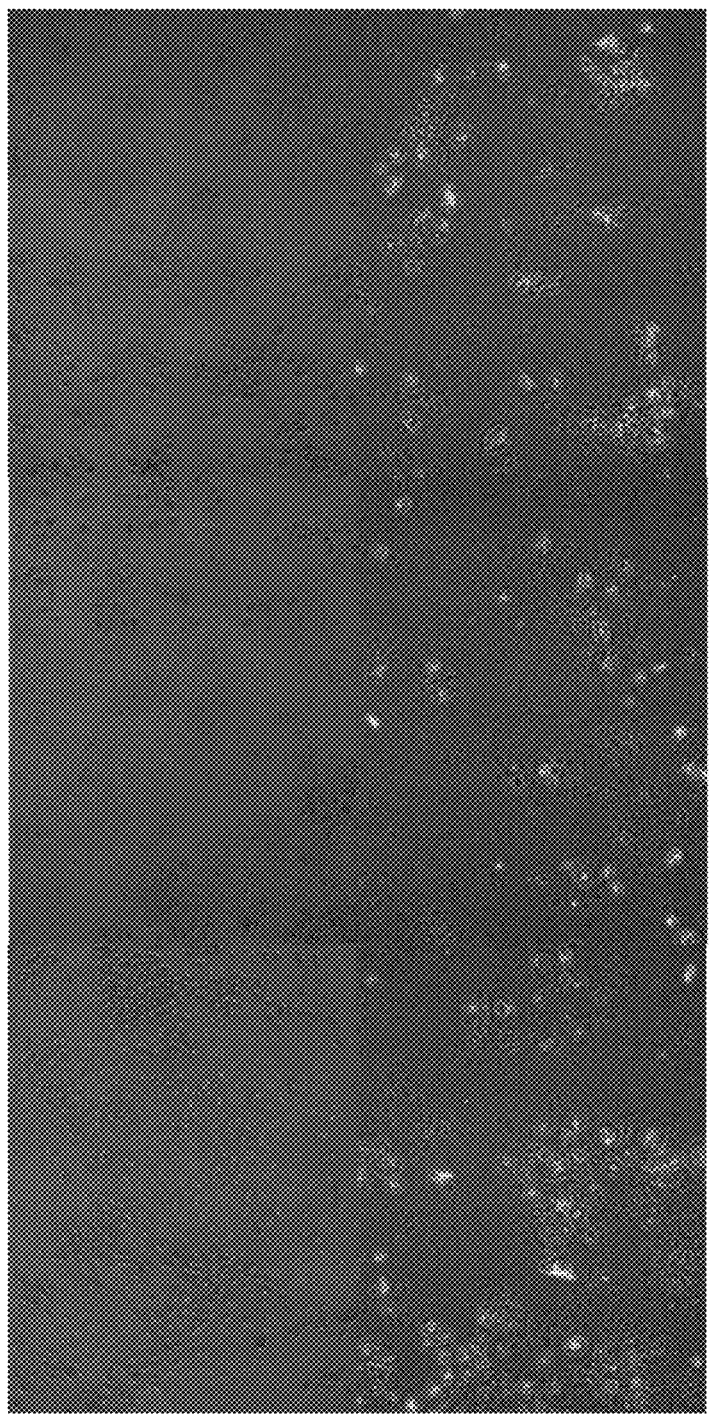

FIG. 21 is a drawing schematically illustrating experimental results 12 hours after the human outer root sheath cells are irradiated with the ultrasound (the pressure: 1.5 MPa and the duty percentage: 10%) in accordance with one example embodiment of the present disclosure.

By referring to FIGS. 20 and 21, compared to the results of the control group, a decrease is observed in the viability of the cells, for example, the cell bursting or the deformation of most of the cells, at the time of the ultrasound irradiation and 12 hours after the ultrasound irradiation (the pressure: 1.5 MPa and the duty percentage: 10%).

As such, by referring to FIGS. 6 to 21, the ultrasound of the pressure of 1 MPa or less, the duty percentage of 5% or less, and the intensity of 416.7 mW/cm$^2$ or less is confirmed to be safe for the cells.

In addition, when the pressure was set to 1.5 MPa or more, the cell bursting or the deformation is observed. Also, compared to the control group, an increase in growth of the cells is observed when the cells are irradiated with the ultrasound in a safe energy range.

As an example, in accordance with the method for increasing the viability of the cells by irradiating the cells with the ultrasound, on condition that the drug and the epidermal drug carrier are applied on epidermis of a subject and that the ultrasound parameters have been preset within respective ranges, the ultrasound irradiating device may position an ultrasonic transducer within a threshold range from the epidermis of the subject and then may irradiate the epidermis with the ultrasound. Herein, the epidermal drug carrier may cause cavitation to create at least one cavity around the epidermis in response to irradiating the epidermis with the ultrasound. Further, the ultrasound parameters may include the pressure of the ultrasound and the duty percentage of the ultrasound. And the pressure of the ultrasound may range from 0.5 MPa to 1 MPa and the duty percentage of the ultrasound may range from 1% to 5%.

Also, the ultrasound parameters may further include the intensity of the ultrasound, which may be in a range from 166.7 mW/cm$^2$ to 416.7 mW/cm$^2$.

Also, the ultrasound parameters may further include a total time of the ultrasound irradiation which may be ten minutes, but the scope of the present disclosure is not limited thereto and the total time of the ultrasound irradiation may be shorter or longer than ten minutes.

In addition, the ultrasonic transducer may irradiate the epidermis of the subject with the ultrasound, in contact with the epidermis or at a certain distance from the epidermis. In addition, the ultrasonic transducer may have a shape surrounding the epidermis of the subject in a form of a helmet or a headgear.

Meanwhile, the ultrasound parameters may further include the frequency of the ultrasound which may range from 0.5 MHz to 4.6 MHz.

As an example, the frequency of the ultrasound may be 1 MHz.

Meanwhile, the drug may be Redensyl and a concentration of the Redensyl may range from 0.5% to 1%.

Also, the cells may be the outer root sheath cells.

FIGS. 22 to 25 are drawings schematically illustrating (i) experimental results of the viability of the human outer root sheath cells derived by only applying the drug of various concentrations and (ii) experimental results of the viability of the human outer root sheath cells derived by applying the drug of the various concentrations together with the epidermal drug carrier and the ultrasound.

Figure 22:
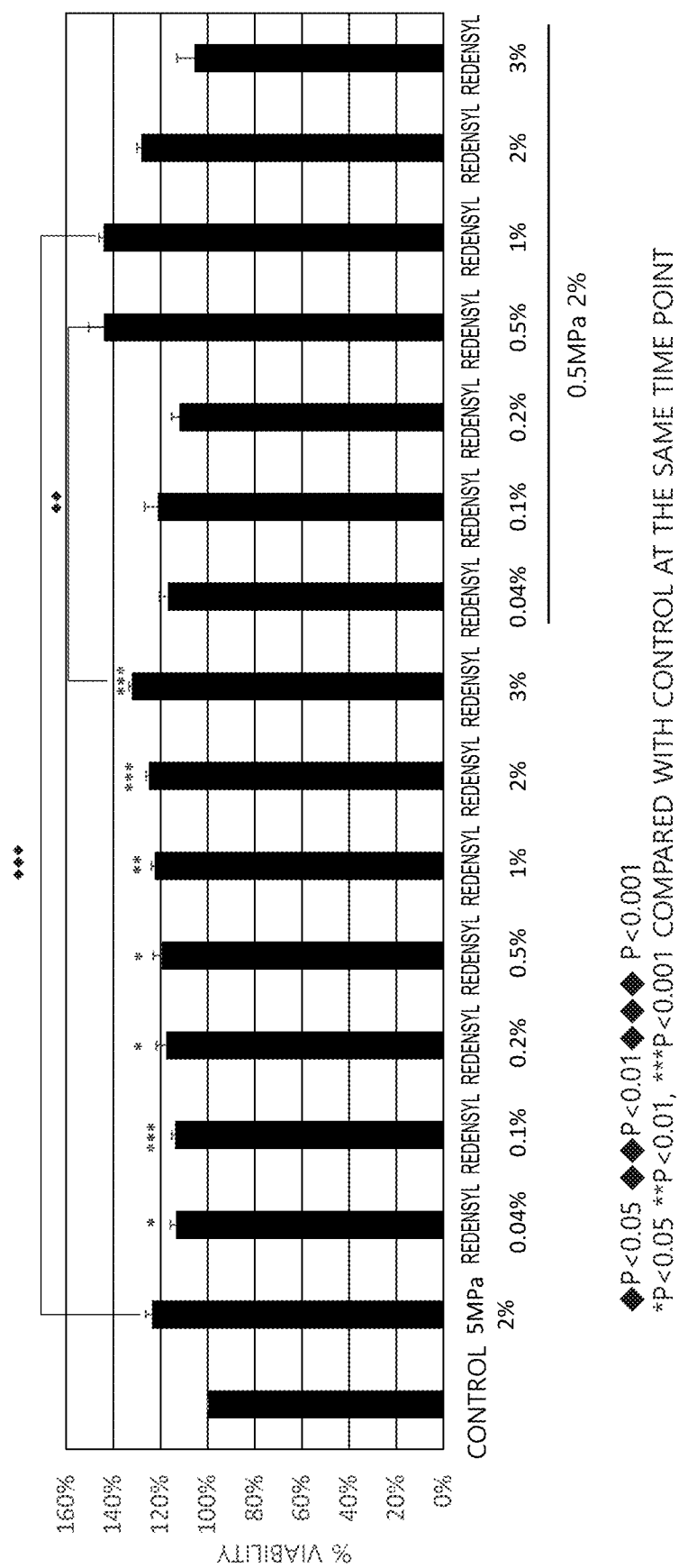
FIGS. 22 to 25 are drawings schematically illustrating comparisons between experimental results of the viability of the human outer root sheath cells in accordance with one example embodiment of the present disclosure and experimental results of the viability of the human outer root sheath cells where only a drug is applied.

As an example, as can be seen in FIG. 22, under a condition of applying the ultrasound of a same intensity (0.5 MPa, 2%), the highest cell viability is observed when the concentration of the drug is 0.5% to 1%.

In addition, when the ultrasound of an appropriate intensity, for example, the ultrasound with the pressure of 0.5 MPa and the duty percentage of 2% is applied together with the drug (0.5% to 1% concentration) and the epidermal drug carrier, a significantly higher viability of the cells is observed compared to a result of only applying the drug of the same concentration.

Figure 23:
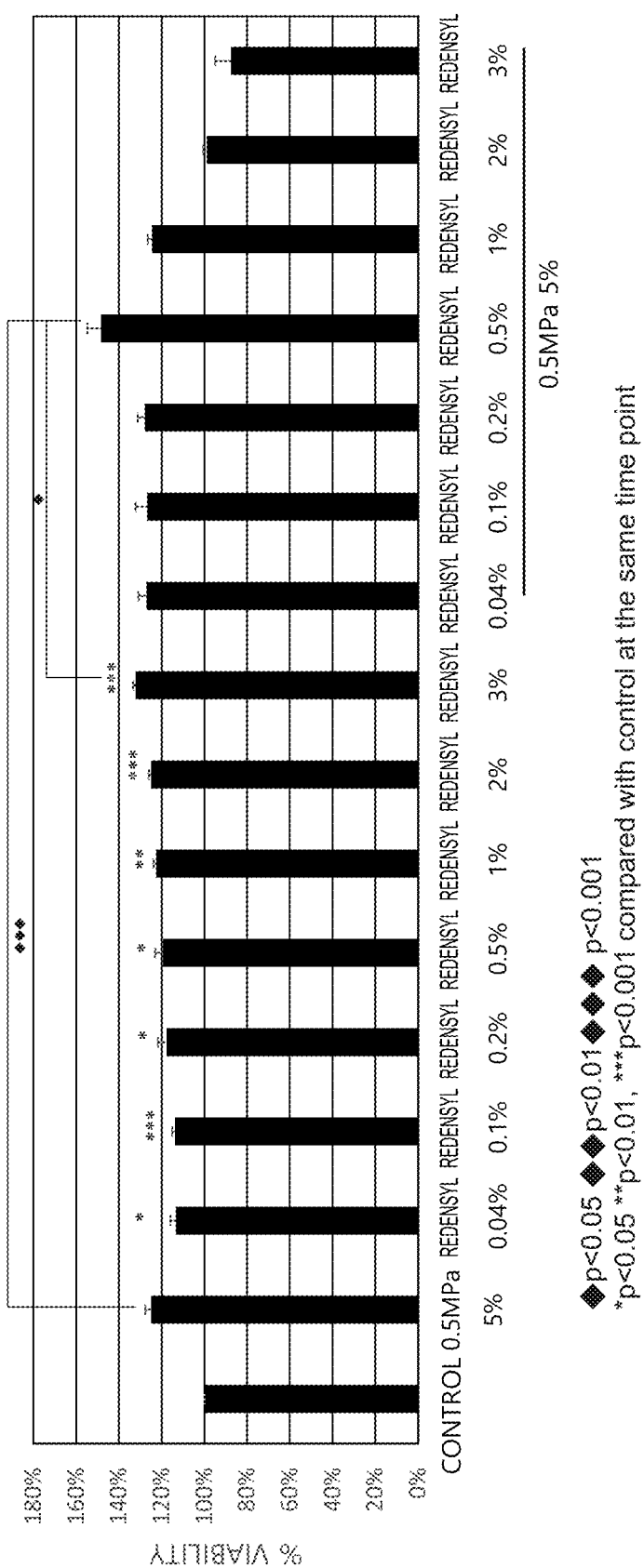
Figure 24:
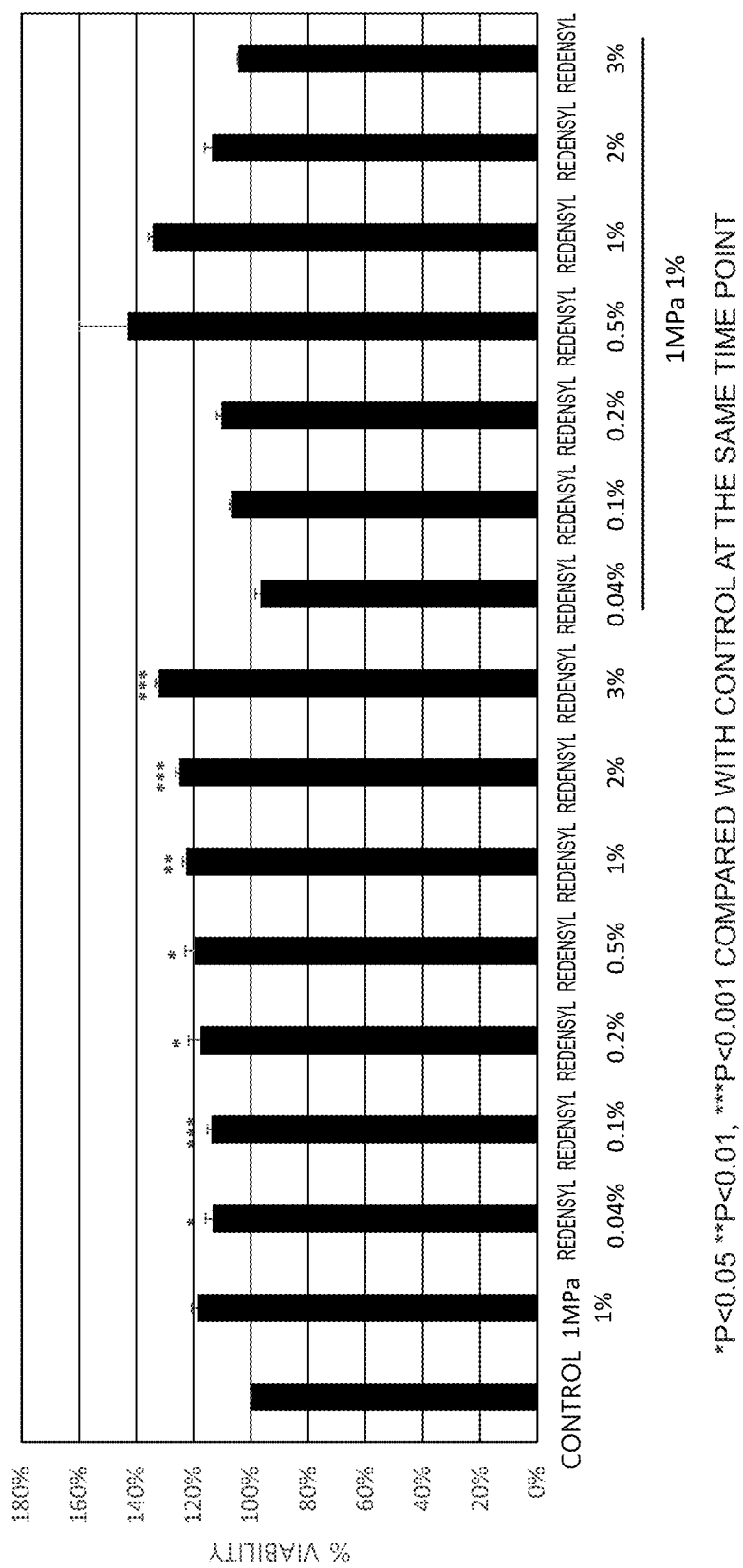

Meanwhile, since description of FIG. 22 is similar to that of FIGS. 23 and 24, detailed description is omitted.

Figure 25:
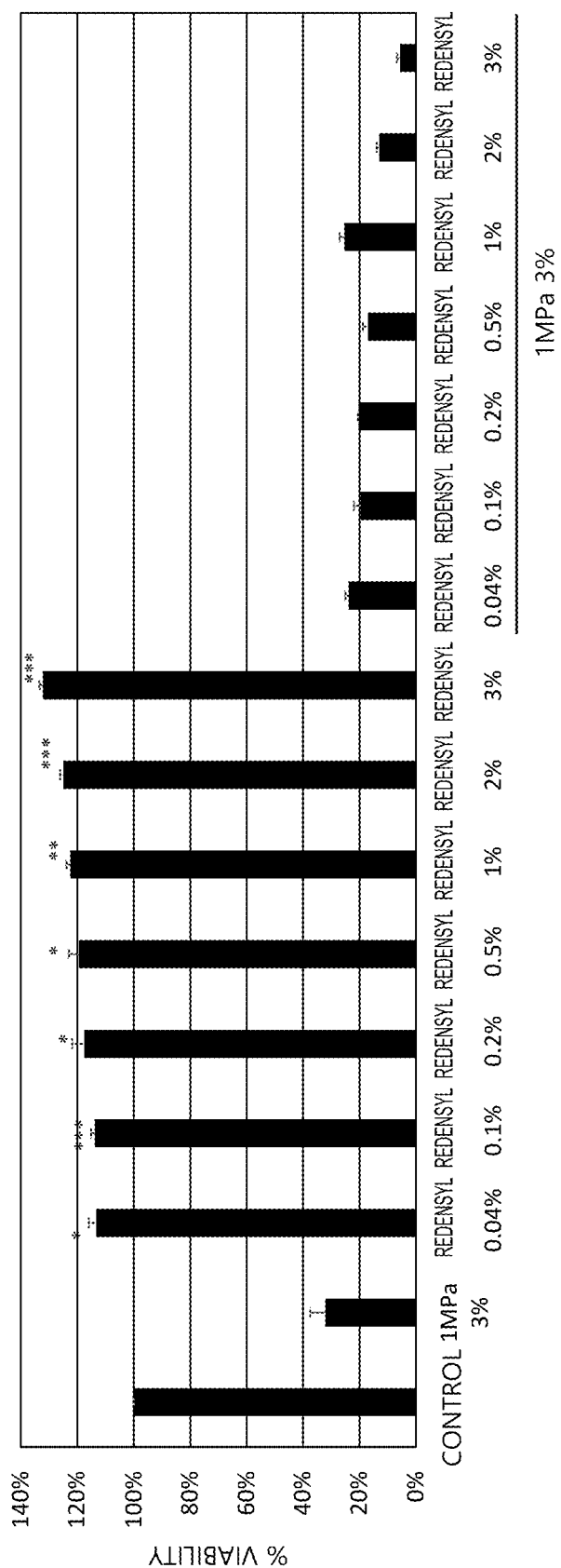
Figure 26:
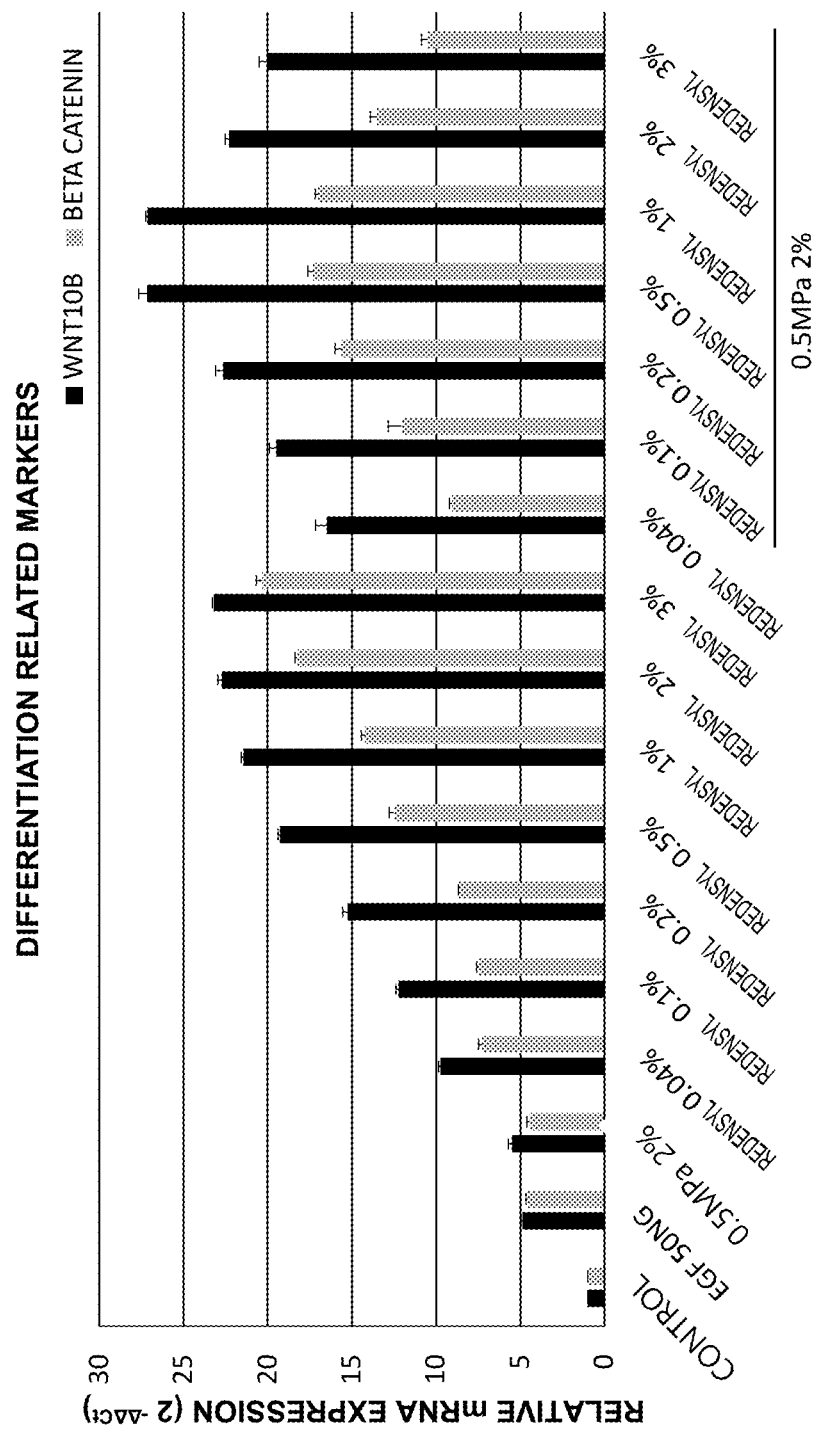
FIGS. 26 to 37 are drawings schematically illustrating experimental results of gene expression in response to irradiating the cells with the ultrasound in accordance with one example embodiment of the present disclosure.
Figure 27:
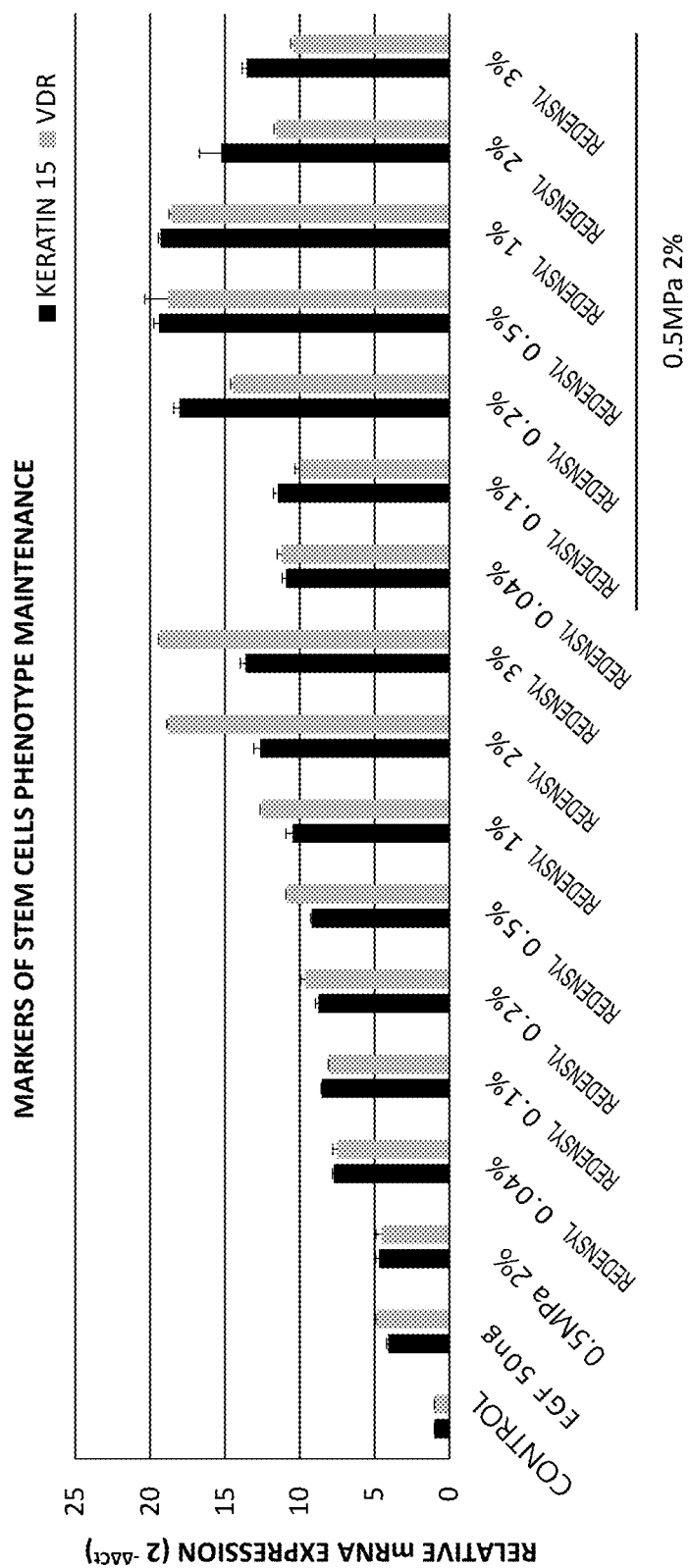
Figure 28:
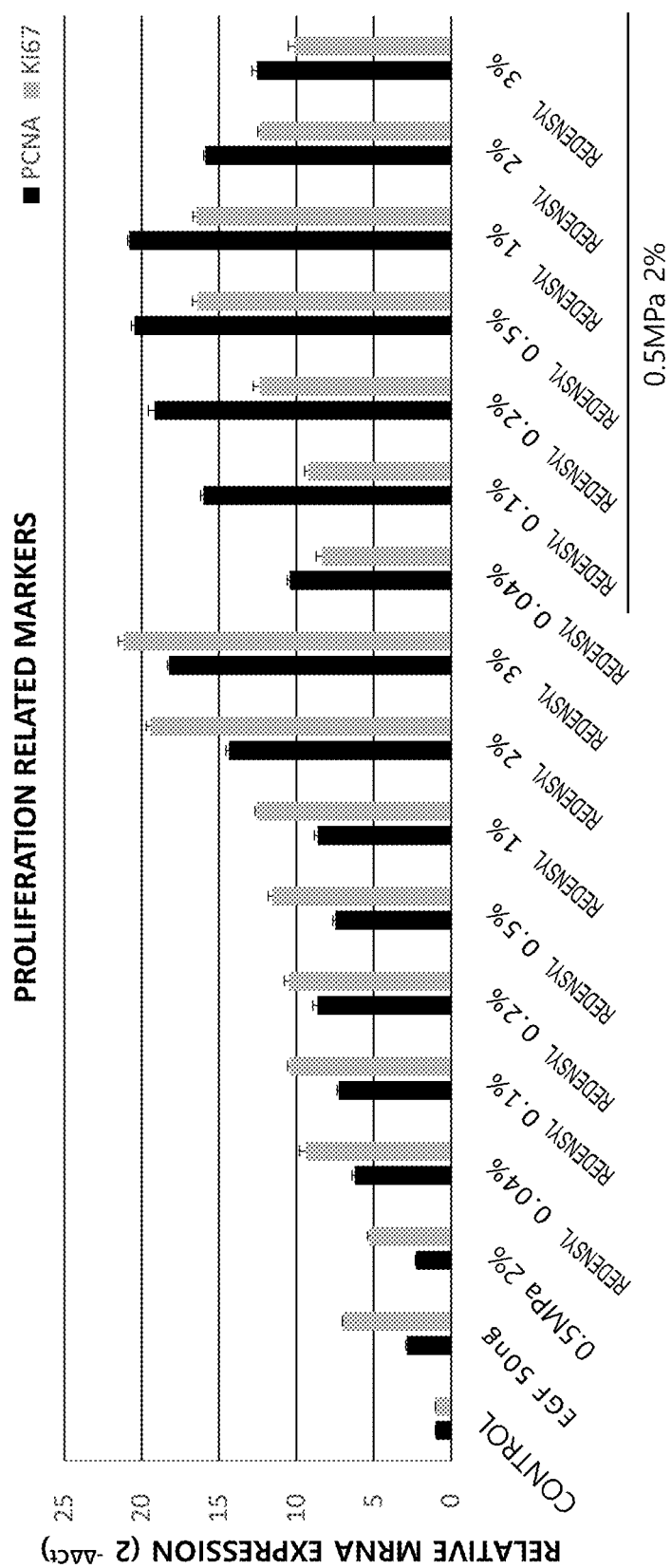
Figure 29:
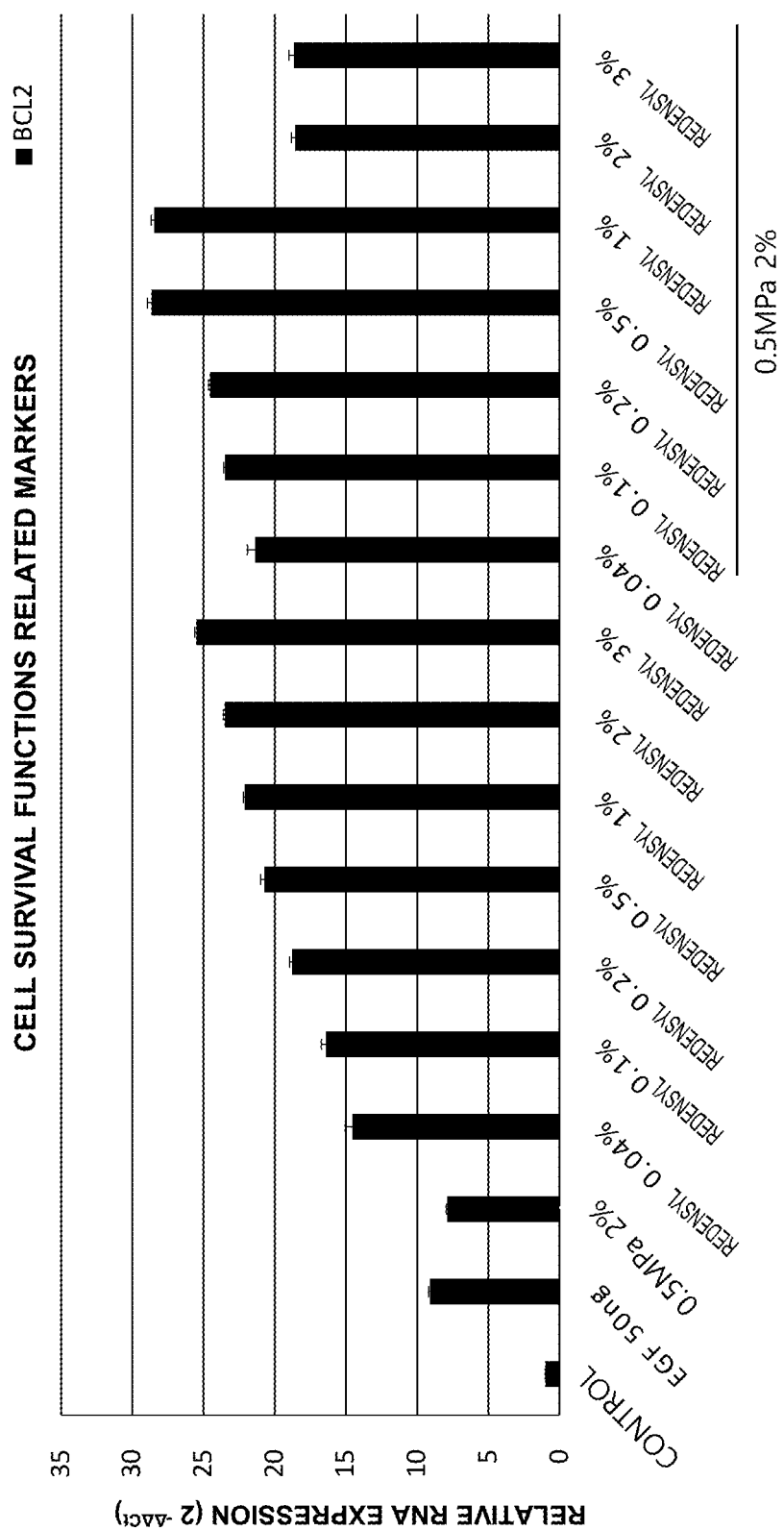
Figure 30:
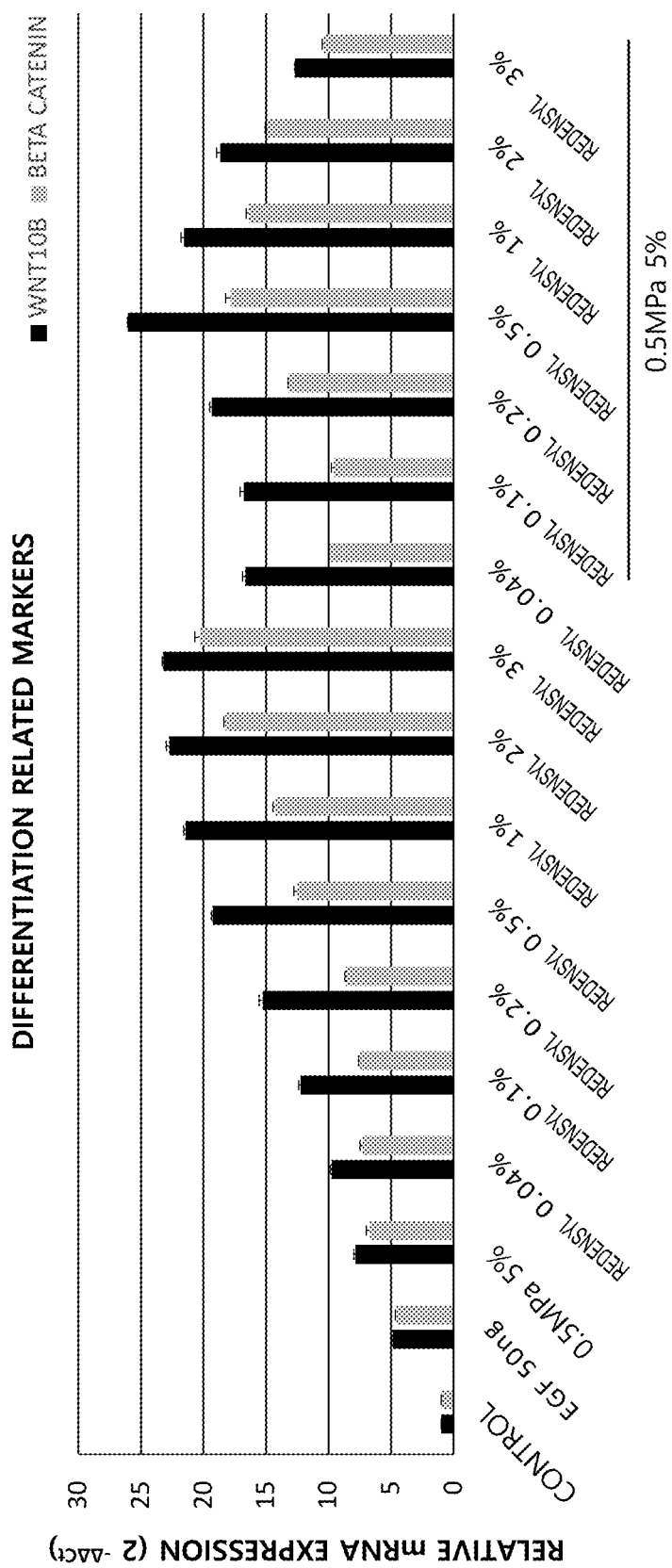
Figure 31:
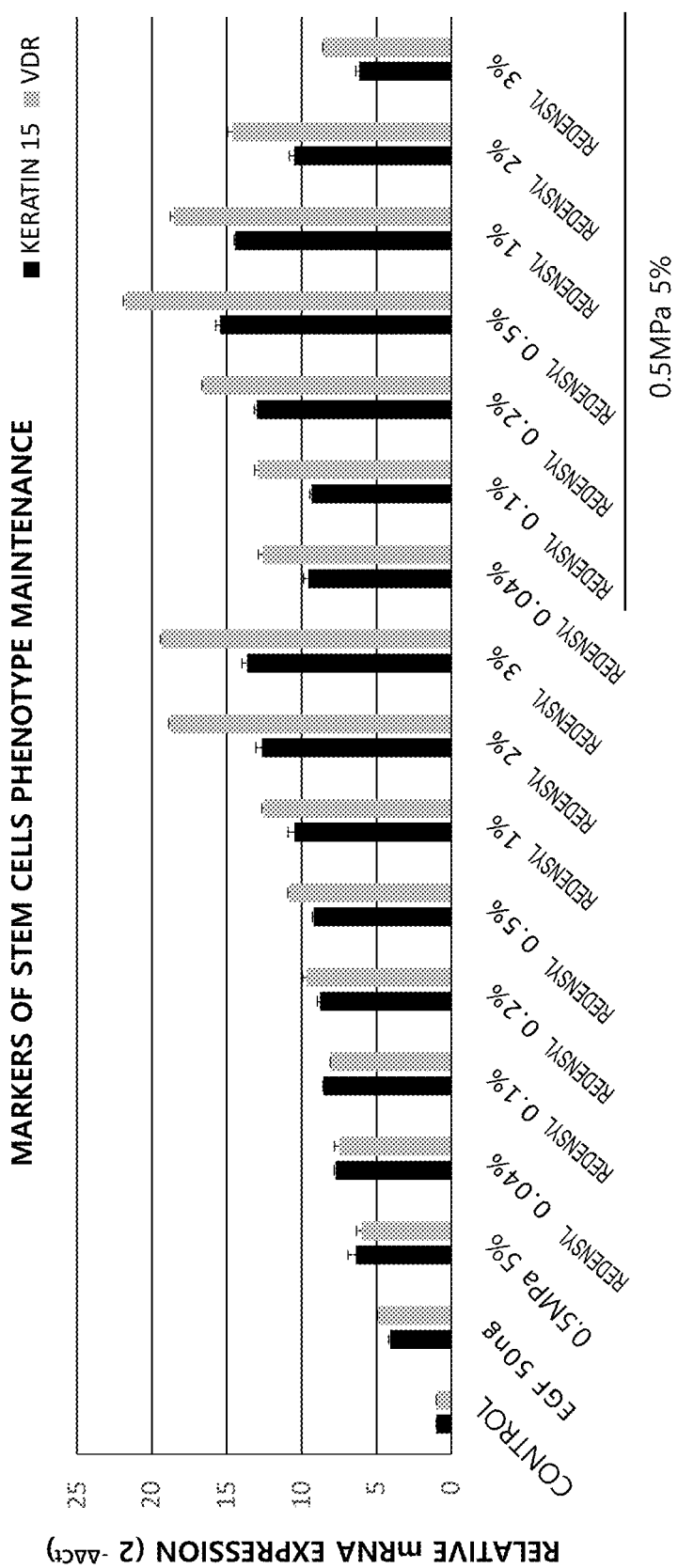
Figure 32:
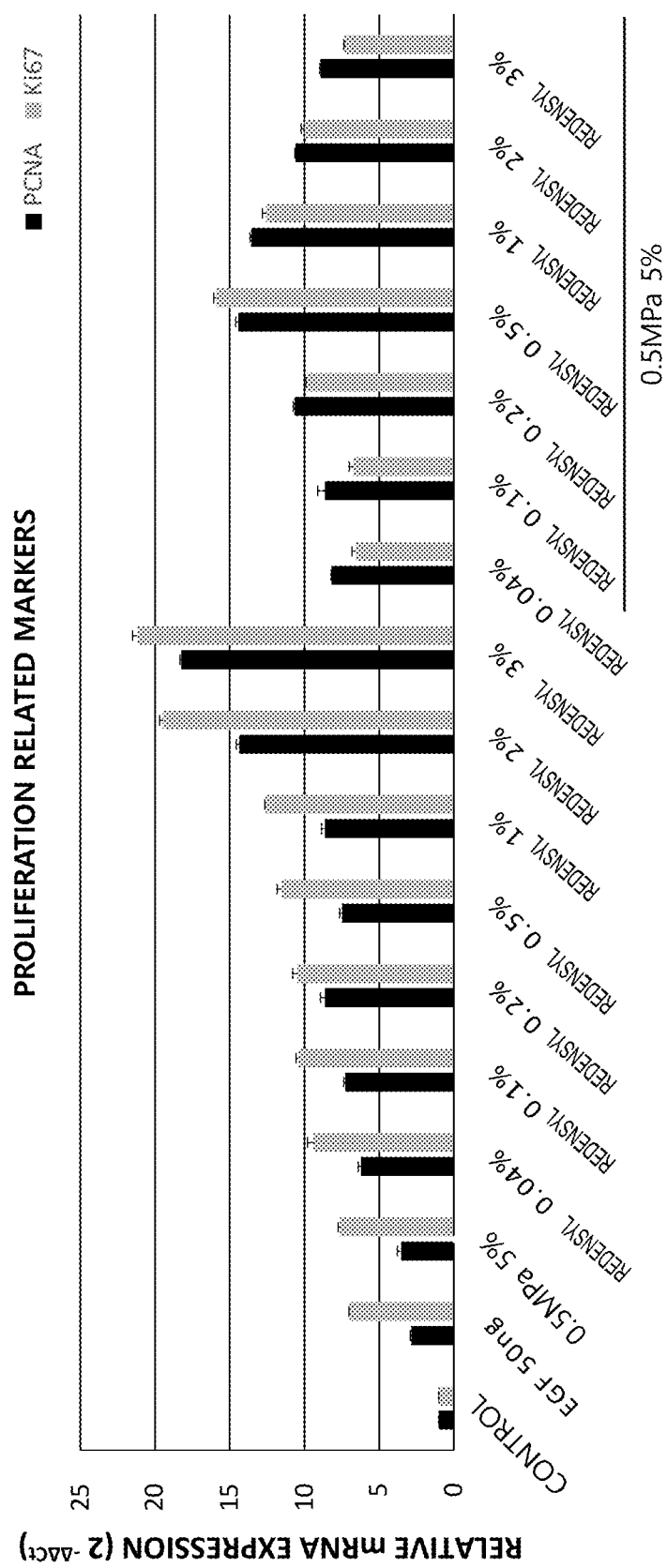
Figure 33:
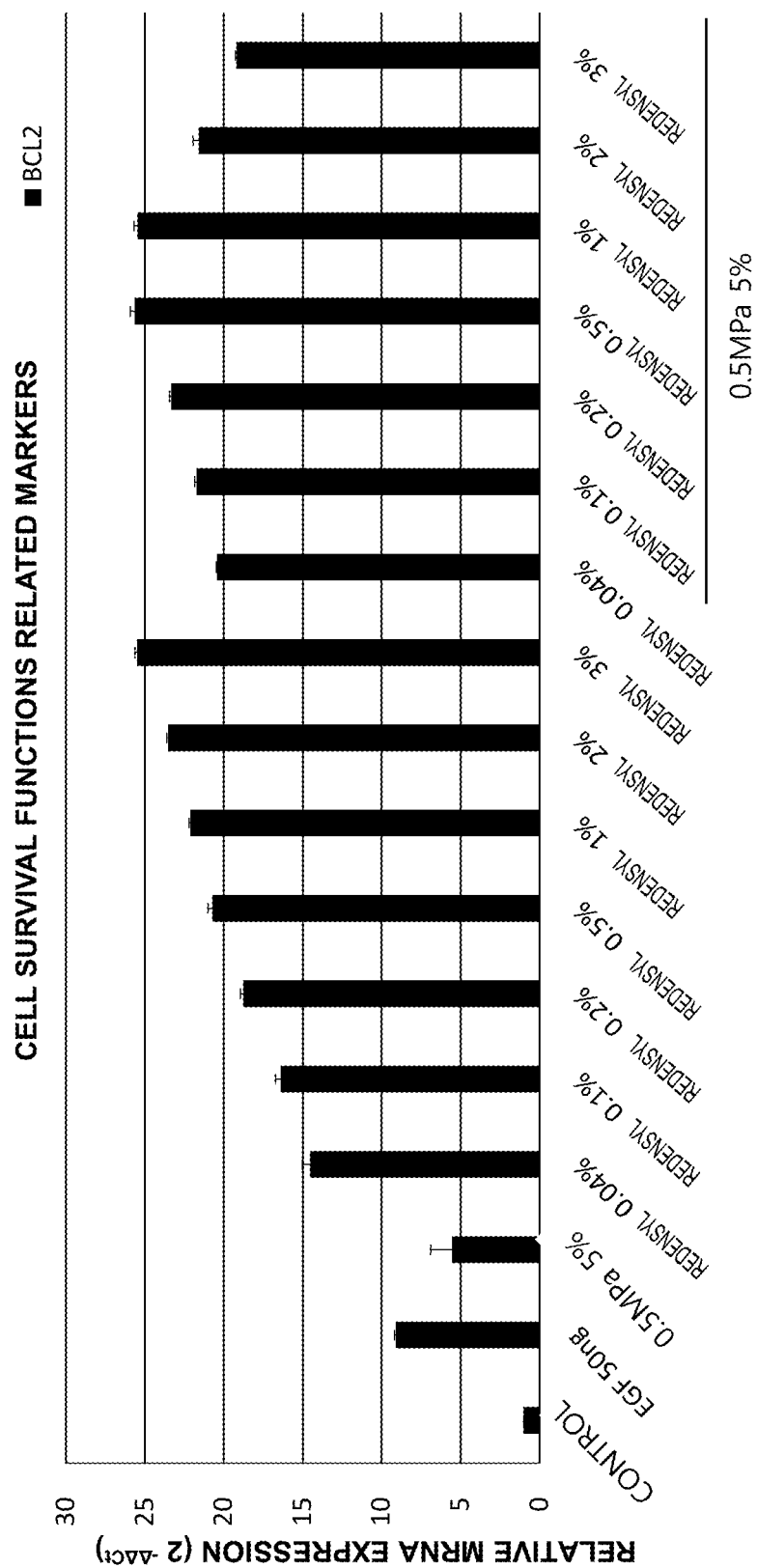
Figure 34:
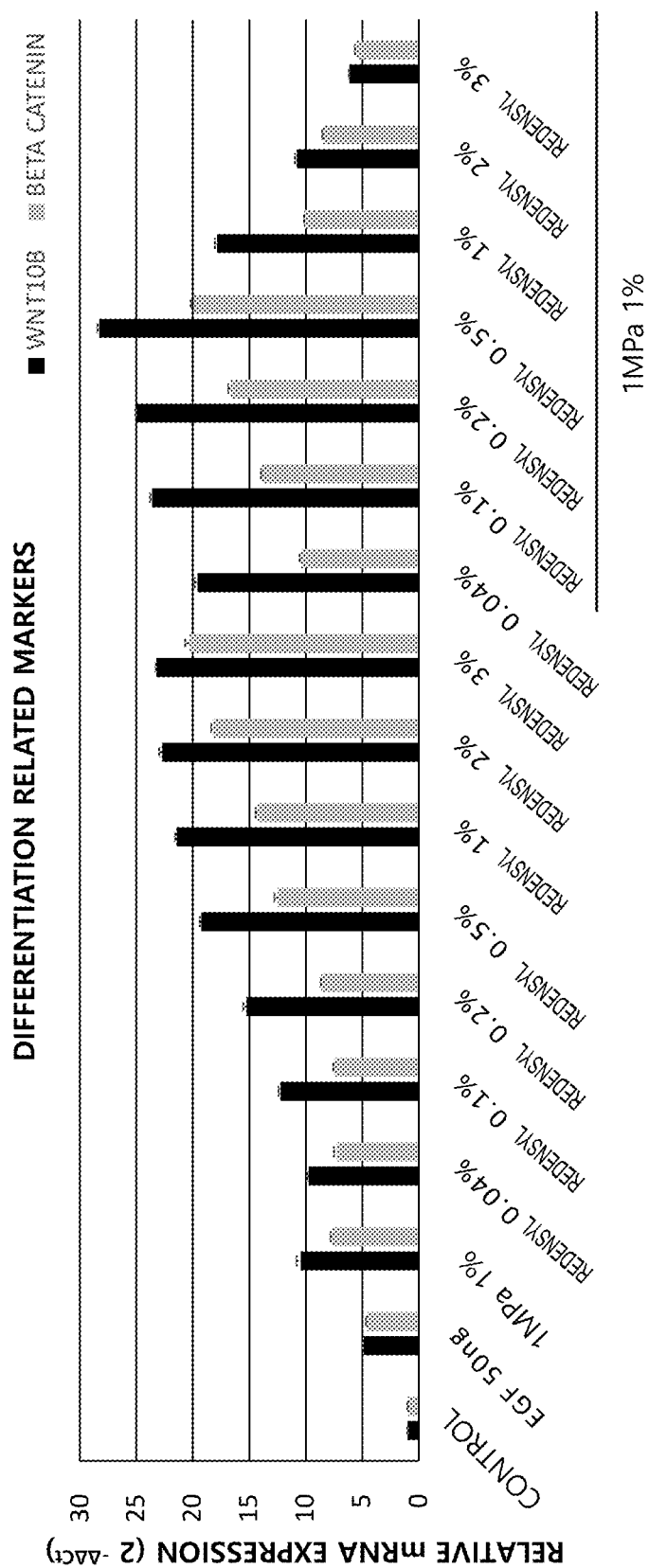
Figure 35:
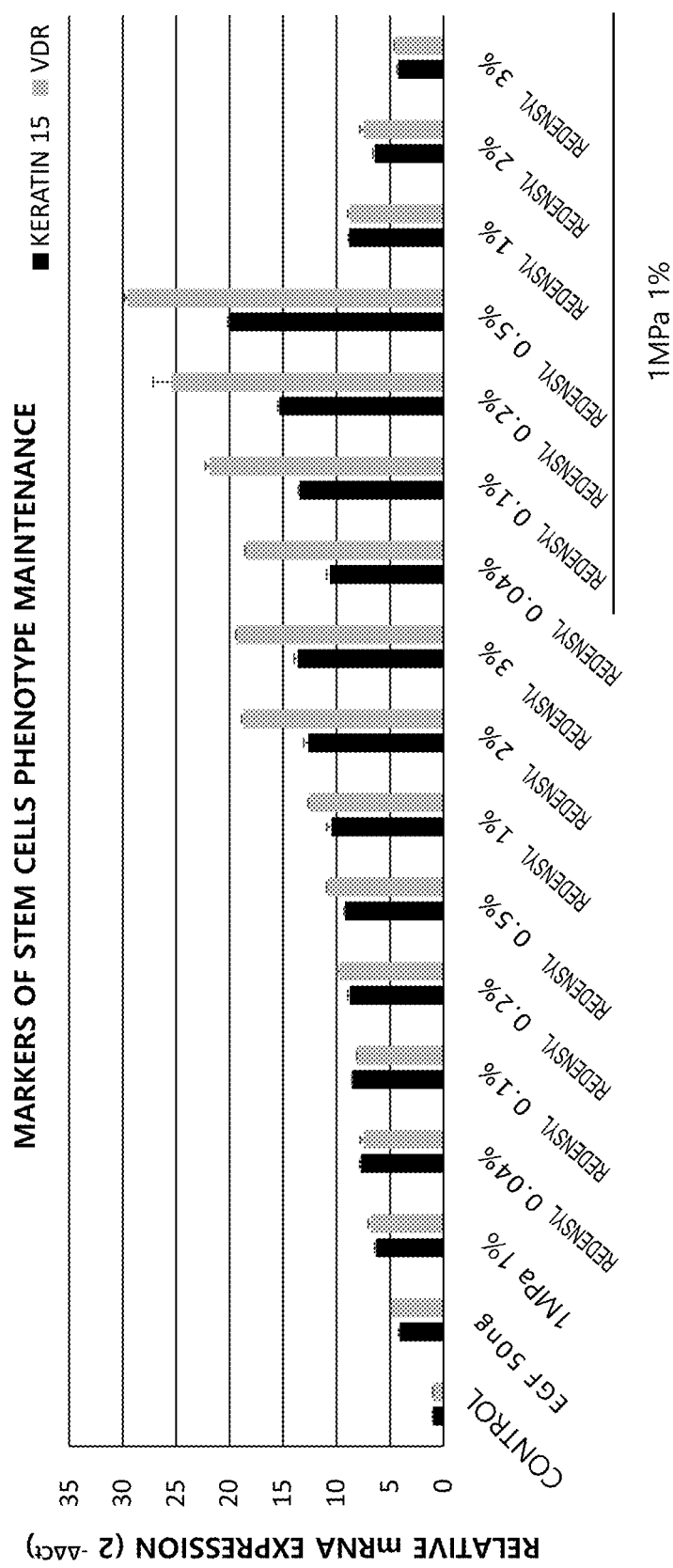
Figure 36:
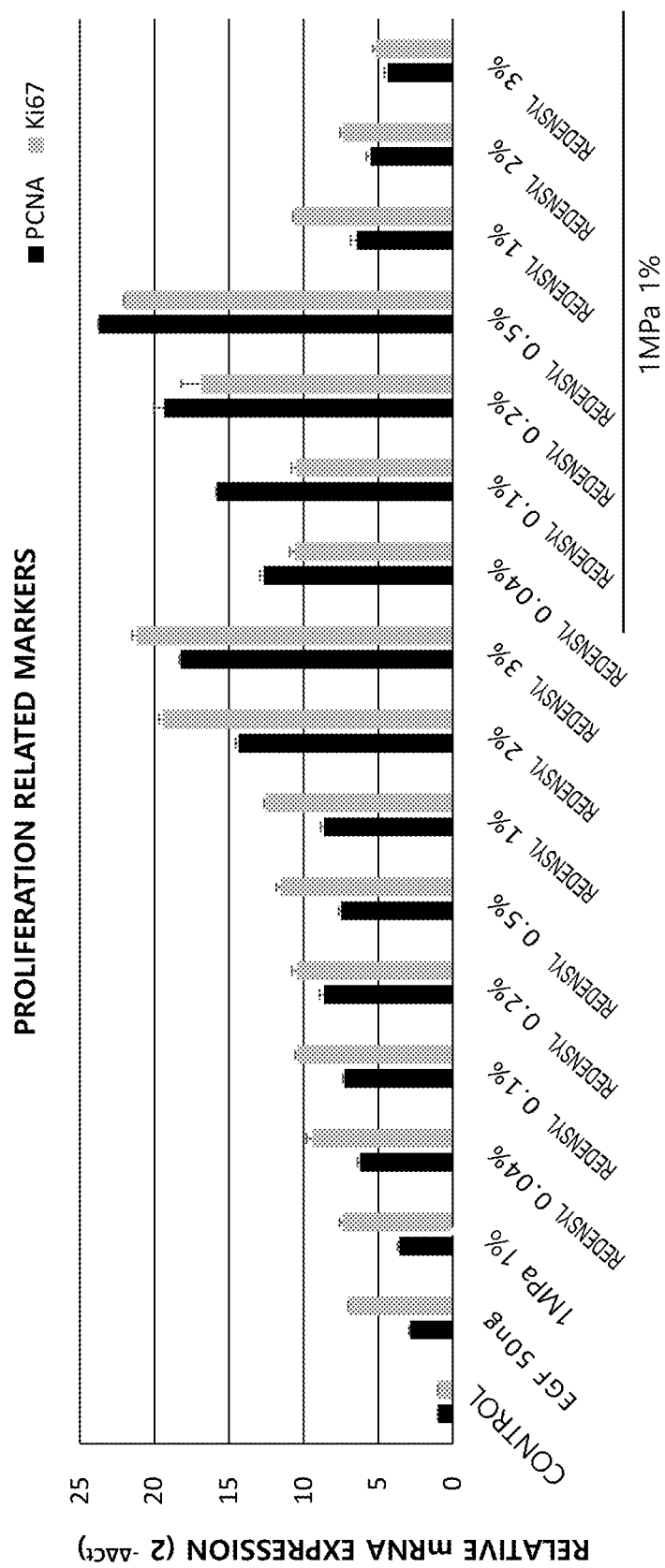
Figure 37:
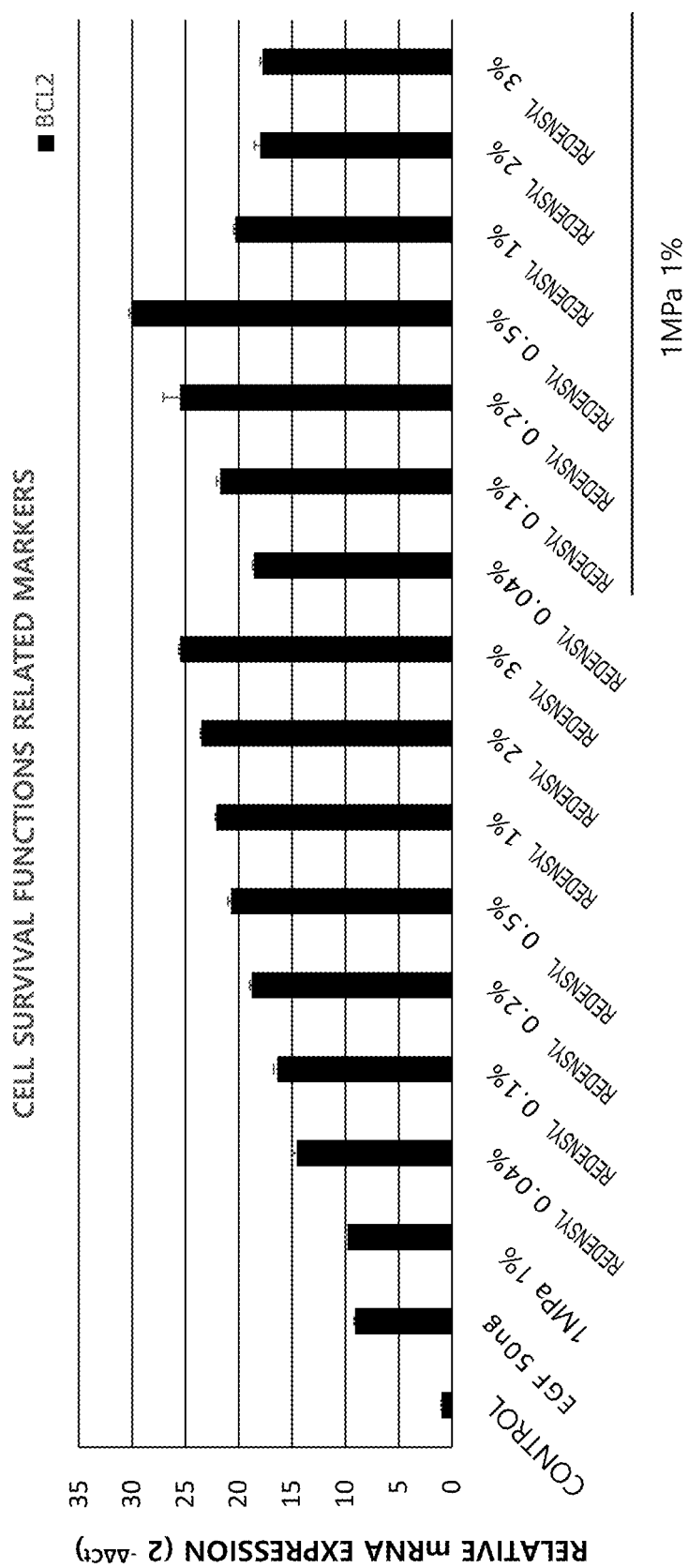

Also, as shown in FIGS. 22 to 24, when the intensity of the ultrasound is 166.7 mW/cm$^2$ (0.5 MPa, 2%), 333.4 mW/cm$^2$ (1 MPa, 1%), and 416.7 mW/cm$^2$ (0.5 MPa, 5%), it is observed that the viability of the cells is significantly higher than that in other ranges of the intensity, for example, as shown in FIG. 25, when the pressure of the ultrasound is 1 MPa and the duty percentage is 3%.

For reference, Tables 11 to 14 below describe the experimental results as shown in FIGS. 22 to 25 respectively.

TABLE 11

|  |  | av | sd |
|---|---|---|---|
| Drug only | Control | 100% | 0.00 |
|  | 0.5 MPa 2% | 124% | 0.03 |
|  | Redensyl 0.04% | 113% | 0.02 |
|  | Redensyl 0.1% | 114% | 0.01 |
|  | Redensyl 0.2% | 118% | 0.04 |
|  | Redensyl 0.5% | 119% | 0.04 |
|  | Redensyl 1% | 123% | 0.01 |
|  | Redensyl 2% | 125% | 0.01 |
|  | Redensyl 3% | 132% | 0.01 |

TABLE 11-continued

|  |  | av | sd |
|---|---|---|---|
| Ultrasound 0.5 MPa 2% + epidermal drug carrier + drug | Redensyl 0.04% | 117% | 0.04 |
|  | Redensyl 0.1% | 121% | 0.05 |
|  | Redensyl 0.2% | 112% | 0.03 |
|  | Redensyl 0.5% | 144% | 0.06 |
|  | Redensyl 1% | 144% | 0.02 |
|  | Redensyl 2% | 128% | 0.02 |
|  | Redensyl 3% | 106% | 0.07 |

TABLE 12

|  |  | av | sd |
|---|---|---|---|
| Drug only | Control | 100% | 0.00 |
|  | 0.5 MPa 5% | 125% | 0.01 |
|  | Redensyl 0.04% | 113% | 0.02 |
|  | Redensyl 0.1% | 114% | 0.01 |
|  | Redensyl 0.2% | 118% | 0.04 |
|  | Redensyl 0.5% | 119% | 0.04 |
|  | Redensyl 1% | 123% | 0.01 |
|  | Redensyl 2% | 125% | 0.01 |
|  | Redensyl 3% | 132% | 0.01 |
| Ultrasound 0.5 MPa 5% + epidermal drug carrier + drug | Redensyl 0.04% | 127% | 0.03 |
|  | Redensyl 0.1% | 127% | 0.04 |
|  | Redensyl 0.2% | 128% | 0.09 |
|  | Redensyl 0.5% | 148% | 0.04 |
|  | Redensyl 1% | 125% | 0.03 |
|  | Redensyl 2% | 99% | 0.05 |
|  | Redensyl 3% | 88% | 0.01 |

TABLE 13

|  |  | av | sd |
|---|---|---|---|
| Drug only | Control | 100% | 0.00 |
|  | 1 MPa 1% | 118% | 0.02 |
|  | Redensyl 0.04% | 113% | 0.02 |
|  | Redensyl 0.1% | 114% | 0.01 |
|  | Redensyl 0.2% | 118% | 0.04 |
|  | Redensyl 0.5% | 119% | 0.04 |
|  | Redensyl 1% | 123% | 0.01 |
|  | Redensyl 2% | 125% | 0.01 |
|  | Redensyl 3% | 132% | 0.01 |
| Ultrasound 1 MPa 1% + epidermal drug carrier + drug | Redensyl 0.04% | 97% | 0.02 |
|  | Redensyl 0.1% | 107% | 0.01 |
|  | Redensyl 0.2% | 110% | 0.02 |
|  | Redensyl 0.5% | 143% | 0.17 |
|  | Redensyl 1% | 134% | 0.01 |
|  | Redensyl 2% | 114% | 0.03 |
|  | Redensyl 3% | 104% | 0.00 |

TABLE 14

|  |  | av | sd |
|---|---|---|---|
| Drug only | Control | 100% | 0.00 |
|  | 1 MPa 3% | 32% | 0.05 |
|  | Redensyl 0.04% | 113% | 0.02 |
|  | Redensyl 0.1% | 114% | 0.01 |
|  | Redensyl 0.2% | 118% | 0.04 |
|  | Redensyl 0.5% | 119% | 0.04 |
|  | Redensyl 1% | 123% | 0.01 |
|  | Redensyl 2% | 125% | 0.01 |
|  | Redensyl 3% | 132% | 0.01 |
| Ultrasound 1 MPa 3% + epidermal drug carrier + drug | Redensyl 0.04% | 24% | 0.01 |
|  | Redensyl 0.1% | 20% | 0.02 |
|  | Redensyl 0.2% | 20% | 0.00 |
|  | Redensyl 0.5% | 17% | 0.02 |
|  | Redensyl 1% | 25% | 0.02 |
|  | Redensyl 2% | 13% | 0.01 |
|  | Redensyl 3% | 6% | 0.01 |

Meanwhile, FIGS. 26 to 37 are drawings schematically illustrating experimental results of gene expression in response to irradiating the cells with the ultrasound in accordance with one example embodiment of the present disclosure.

Specifically, FIGS. 26 to 37 are drawings schematically illustrating the experimental results of the gene expression related to WNT10B, Beta Catenin, Keratin 15, VDR, PCNA, Ki67 and BCL2 when the drugs are applied to the epidermis of the subject and the epidermis is irradiated with the ultrasound having the frequency of 1 MHz.

As an example, by referring to FIGS. 26 to 29, when the intensity of the ultrasound is set to 166.7 mW/cm$^2$ (0.5 MPa, 2%), the frequency of the ultrasound is set to 1 MHz, and the concentration of Redensyl is at 0.5% to 1%, it is observed that the gene expression levels related to WNT10B, Beta Catenin, Keratin 15, VDR, PCNA, Ki67 and BCL2 are significantly higher than those in other ranges of the ultrasound.

FIGS. 30 to 33 show a case where the intensity of the ultrasound is set to 416.7 mW/cm$^2$ (0.5 MPa, 5%), the frequency of the ultrasound is set to 1 MHz. And similar to description of FIGS. 26 to 29, it is observed that the gene expression levels related to WNT10B, Beta Catenin, Keratin 15, VDR, PCNA, Ki67 and BCL2 are significantly higher in a range, where the concentration of Redensyl is at 0.5% to 1%, than those in other ranges of the ultrasound.

FIGS. 34 to 37 show a case where the intensity of the ultrasound is set to 333.4 mW/cm$^2$ (1 MPa, 1%), the frequency of the ultrasound is set to 1 MHz. And similar to description of FIGS. 26 to 29, it is observed that the gene expression levels related to WNT10B, Beta Catenin, Keratin 15, VDR, PCNA, Ki67 and BCL2 are significantly higher in a range, where the concentration of Redensyl is at 0.5% to 1%, than those in other ranges of the ultrasound.

Figure 38:
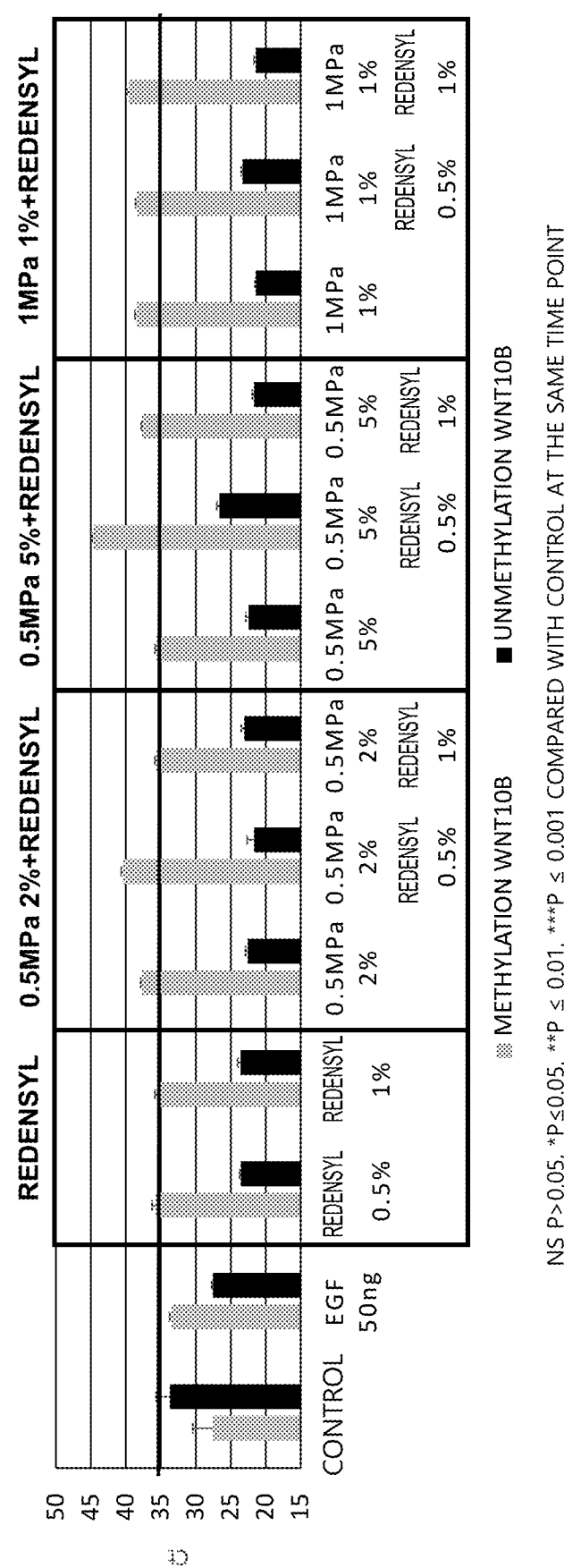
FIGS. 38 to 41 are drawings schematically illustrating degrees of DNA methylation in response to irradiating the cells with the ultrasound in accordance with one example embodiment of the present disclosure.
Figure 39:
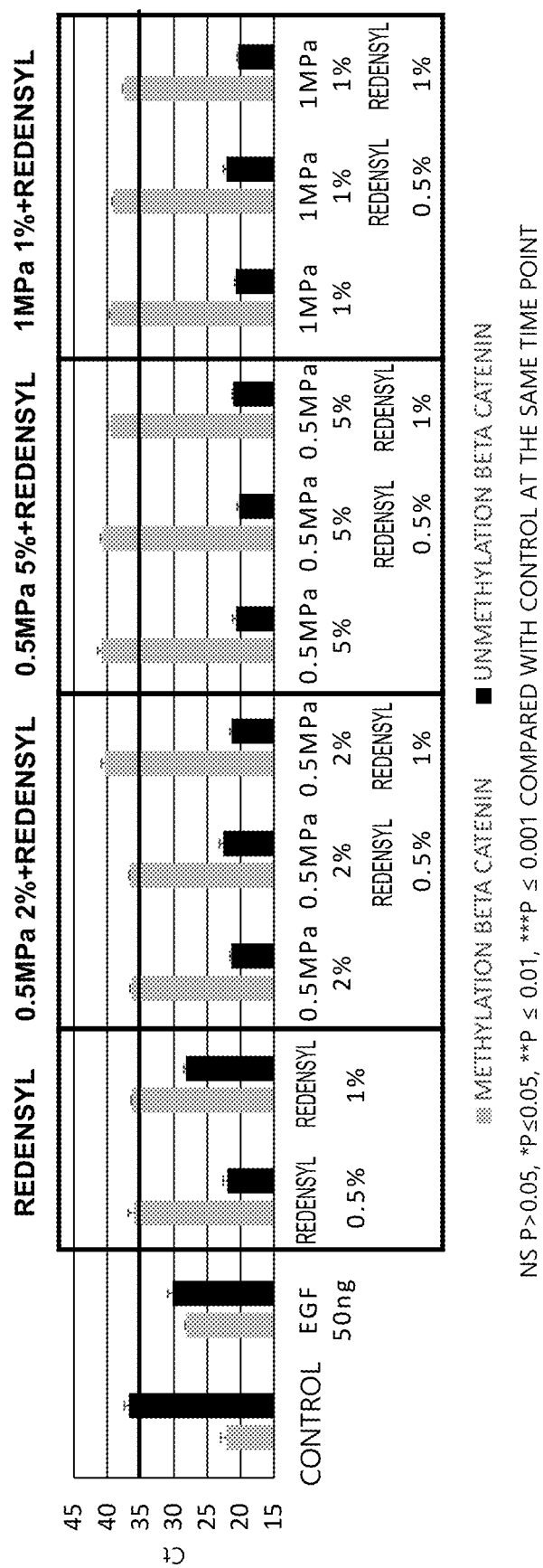
Figure 40:
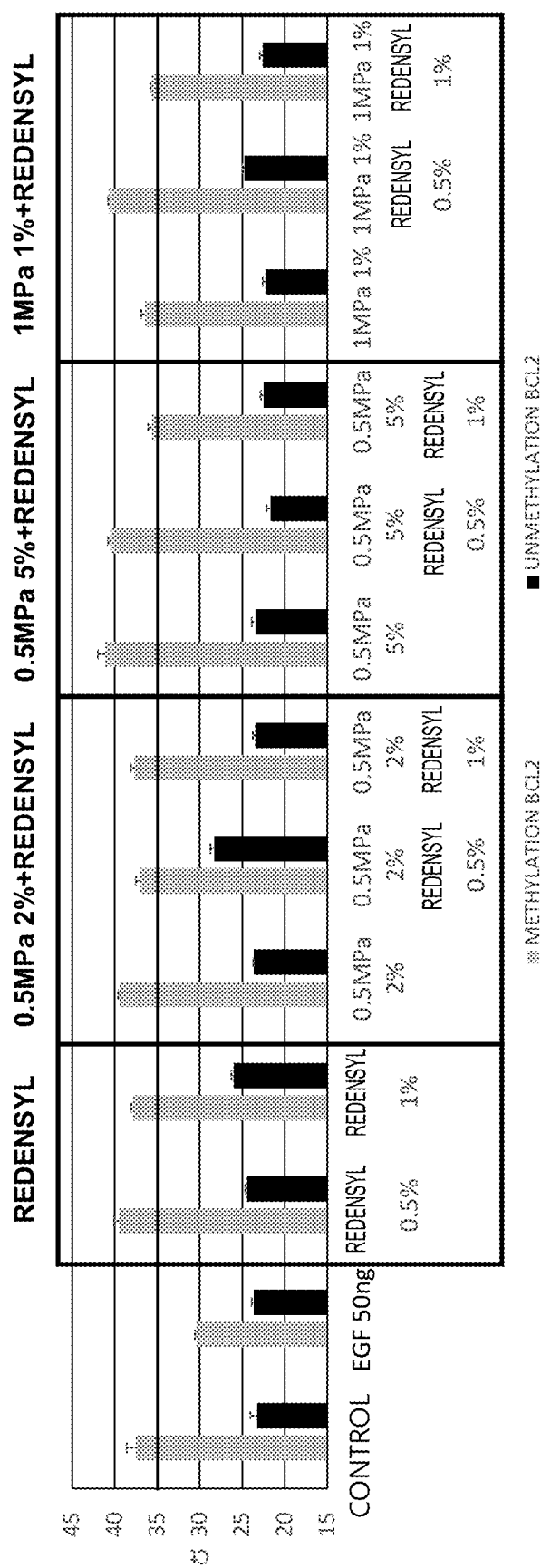
Figure 41:
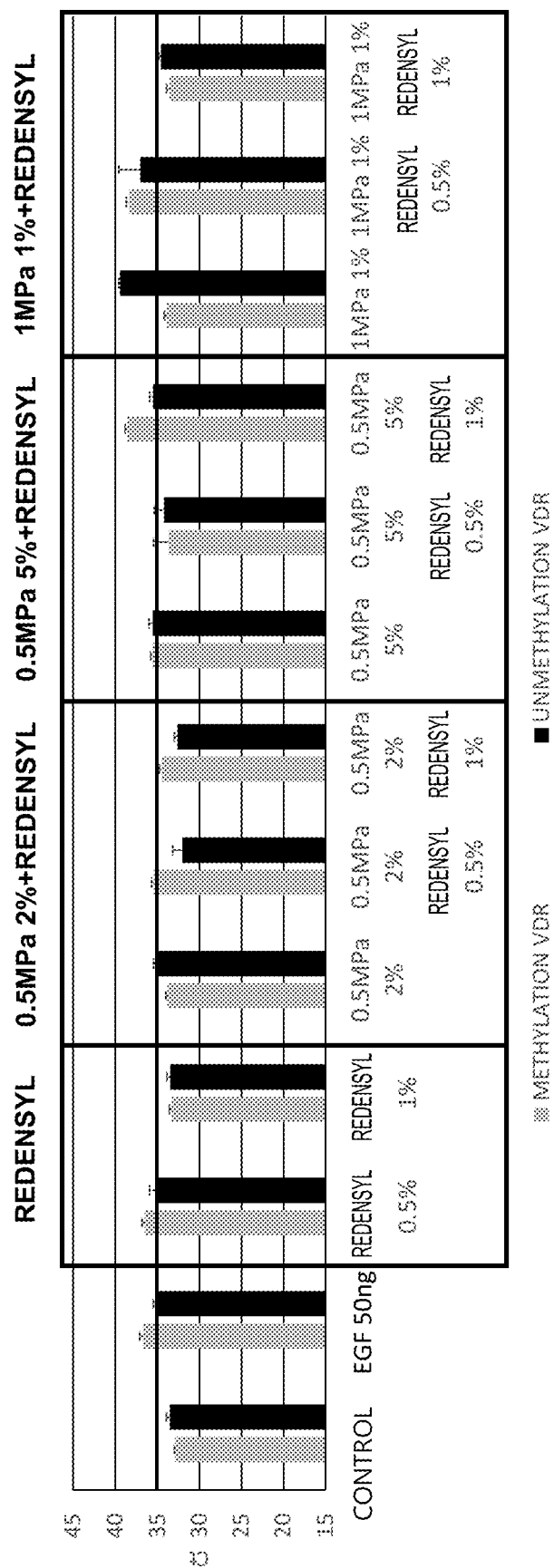

Meanwhile, FIGS. 38 and 39 are drawings schematically illustrating degrees of DNA methylation in response to irradiating the cells with the ultrasound having the frequency of 1 MHz in accordance with one example embodiment of the present disclosure.

As can be seen by referring to FIGS. 38 and 39, when the ultrasound with the frequency of 1 MHz and the intensity of 166.7 mW/cm$^2$ to 416.7 mW/cm$^2$ is applied together with the drug having a concentration of 0.5% to 1% and the epidermal drug carrier, it is observed that the unmethylated DNA Ct values were significantly lowered.

Meanwhile, the ultrasound parameters may further include PRF or PRP. Herein, PRF may range from 1 Hz to 100 Hz and PRP may range from 0.01 second to 1 second.

Figure 42:
FIG. 42 is a drawing schematically illustrating clinical results according to a lapse of time when the epidermal drug carrier, the drug, and the ultrasound are applied together for 10 minutes two times a week in accordance with one example embodiment of the present disclosure.

Meanwhile, FIG. 42 is a drawing schematically illustrating clinical results according to a lapse of time when the epidermal drug carrier, the drug, and the ultrasound are applied together for 10 minutes two times a week in accordance with one example embodiment of the present disclosure.

Figure 43A:
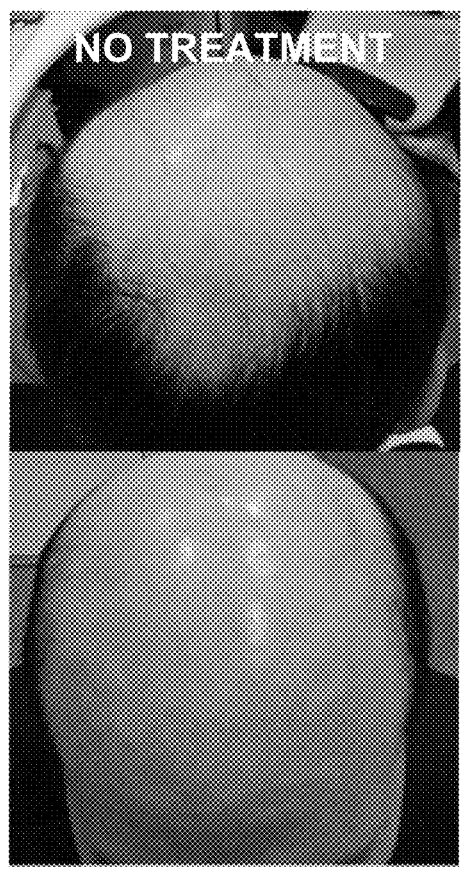
FIG. 43A is a drawing schematically illustrating a case where no treatment is applied.
Figure 43B:
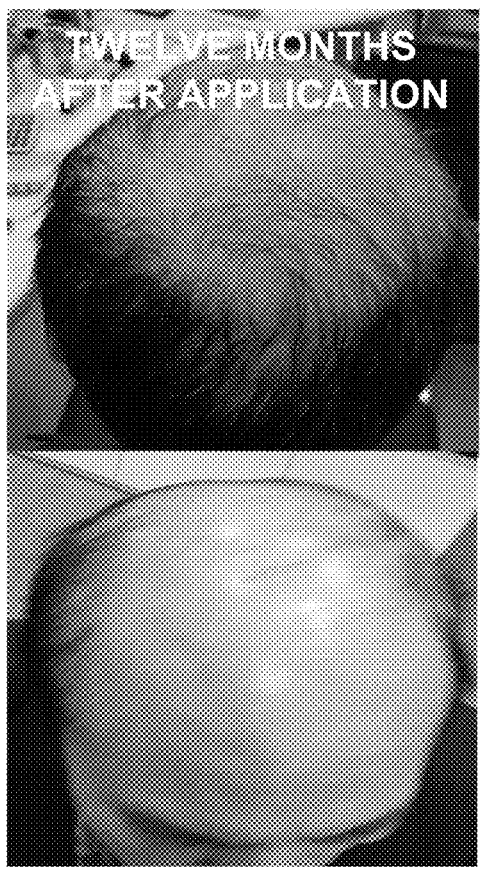
FIG. 43B is a drawing schematically illustrating a case where a conventional treatment is applied for 12 months.
Figure 43C:
FIGS. 43C and 43D are drawings schematically illustrating clinical results according to a lapse of time when the epidermal drug carrier, the drug, and the ultrasound are applied together in accordance with one example embodiment of the present disclosure.
Figure 43D:
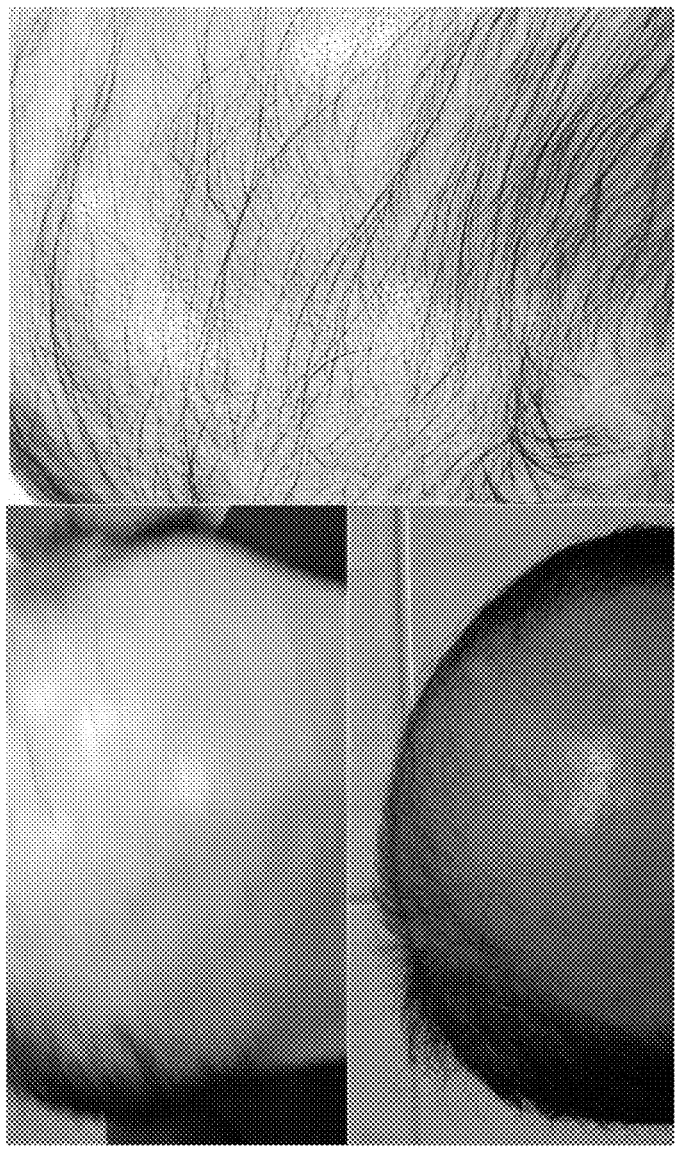

FIG. 43A is a drawing schematically illustrating a case where no treatment is applied. FIG. 43B is a drawing schematically illustrating a case where a conventional treatment is applied for 12 months. FIGS. 43C and 43D are drawings schematically illustrating clinical results according to a lapse of time when the epidermal drug carrier, the drug, and the ultrasound are applied together in accordance with one example embodiment of the present disclosure.

As compared with FIG. 43A, improved results can be confirmed also in FIG. 43B. Further, in FIG. 43B, when compared with FIGS. 43C and 43D, it is observed that there is a very large difference in a time of application. That is, in accordance with the present disclosure, a result same as or superior to that of conventional techniques is acquired within the time of the application (2 to 4 months in case of FIGS. 43C and 43D) remarkably shorter than that (12 months in case of FIG. 43B) of the conventional techniques.

Figure 44A:
FIGS. 44A and 44B are drawings schematically illustrating clinical results according to a lapse of time before and after the epidermal drug carrier, the drug, and the ultrasound are applied together in accordance with one example embodiment of the present disclosure.
Figure 44B:

FIGS. 44A and 44B are drawings schematically illustrating clinical results according to a lapse of time before and after the epidermal drug carrier, the drug, and the ultrasound are applied together for 6 months in accordance with one example embodiment of the present disclosure.

Even with naked eye, the difference between before and after the application can be seen in the number of hairs, etc.

The present disclosure has an effect of increasing the viability of the cells in a non-invasive and painless manner by irradiating the cells with the ultrasound.

The present disclosure has another effect of further increasing the viability of the cells by using the drug together with the epidermal drug carrier and the ultrasound compared to a case of only using the drug with a same concentration.

As seen above, the present disclosure has been explained by specific matters such as detailed components, limited embodiments, and drawings. They have been provided only to help more general understanding of the present disclosure. It, however, will be understood by those skilled in the art that various changes and modification may be made from the description without departing from the spirit and scope of the disclosure as defined in the following claims.

Accordingly, the spirit of the present disclosure must not be confined to the explained embodiments, and the following patent claims as well as everything including variations equal or equivalent to the patent claims pertain to the category of the spirit of the present disclosure.

What is claimed is:

1. A method for increasing a viability of one or more cells by irradiating the cells with ultrasound, comprising a step of:
   on condition that a drug and an epidermal drug carrier are applied on epidermis of a subject and that ultrasound parameters have been preset within respective ranges, an ultrasound irradiating device positioning an ultrasonic transducer within a threshold range from the epidermis of the subject and then irradiating the epidermis with the ultrasound,
   wherein the epidermal drug carrier causes cavitation to create at least one cavity around the epidermis in response to irradiating the epidermis with the ultrasound, and
   wherein the ultrasound parameters include pressure of the ultrasound and duty percentage of the ultrasound, wherein the pressure of the ultrasound ranges from 0.5 MPa to 1 MPa, and wherein the duty percentage of the ultrasound ranges from 1% to 5%,
   wherein, the ultrasound parameters further include a pressure of the ultrasound, a duty percentage of the ultrasound, and an intensity of the ultrasound, and wherein the pressure ranges from 0.5 MPa to 1 MPa, the duty percentage ranges from 1% to 5%, and the intensity ranges from 166.7 mW/cm$^2$ to 416.7 mW/cm$^2$,
   wherein, the ultrasound parameters further include a frequency of the ultrasound, and wherein the frequency of the ultrasound ranges from 0.5 MHz to 4.6 MHZ,
   wherein, the ultrasound parameters further include a total irradiation time of the ultrasound, and wherein the total irradiation time is equal to or less than ten minutes.

2. The method of claim 1, wherein the drug is Redensyl.

3. The method of claim 2, wherein a concentration of the Redensyl ranges from 0.5% to 1%.

4. The method of claim 1, wherein the frequency of the ultrasound is 1 MHz.

5. The method of claim 1, wherein the cells are outer root sheath cells.

6. An ultrasound irradiating device for increasing a viability of one or more cells by irradiating the cells with ultrasound, comprising:
- an ultrasound transducer; and
- a controlling part, on condition that a drug and an epidermal drug carrier are applied on epidermis of a subject and that ultrasound parameters have been preset within respective ranges, for positioning the ultrasonic transducer within a threshold range from the epidermis of the subject and then allowing the ultrasonic transducer to irradiate the epidermis with the ultrasound; and
- wherein the epidermal drug carrier causes cavitation to create at least one cavity around the epidermis in response to irradiating the epidermis with the ultrasound, and
- wherein the ultrasound parameters include a pressure of the ultrasound and a duty percentage of the ultrasound, wherein the pressure of the ultrasound ranges from 0.5 MPa to 1 MPa, and wherein the duty percentage of the ultrasound ranges from 1% to 5%,
- wherein, the ultrasound parameters further include a pressure of the ultrasound, a duty percentage of the ultrasound, and an intensity of the ultrasound, and wherein the pressure ranges from 0.5 MPa to 1 MPa, the duty percentage ranges from 1% to 5%, and the intensity ranges from 166.7 $mW/cm^2$ to 416.7 $mW/cm^2$,
- wherein, the ultrasound parameters further include frequency of the ultrasound, and wherein the frequency of the ultrasound ranges from 0.5 MHz to 4.6 MHZ,
- wherein, the ultrasound parameters further include total irradiation time of the ultrasound, and wherein the total irradiation time is equal to or less than ten minutes.

7. The ultrasound irradiating device of claim 6, wherein the drug is Redensyl.

8. The ultrasound irradiating device of claim 7, wherein a concentration of the Redensyl ranges from 0.5% to 1%.

9. The ultrasound irradiating device of claim 6, wherein the frequency of the ultrasound is 1 MHz.

10. The ultrasound irradiating device of claim 6, wherein the cells are outer root sheath cells.

* * * * *